United States Patent [19]
Okumura

[11] Patent Number: 6,094,498
[45] Date of Patent: Jul. 25, 2000

[54] FACE IMAGE PROCESSING APPARATUS EMPLOYING TWO-DIMENSIONAL TEMPLATE

[75] Inventor: Tomoko Okumura, Tokyo, Japan

[73] Assignee: Mitsubishi Denki Kabushiki Kaisha, Tokyo, Japan

[21] Appl. No.: 09/449,610

[22] Filed: Nov. 30, 1999

[30]     Foreign Application Priority Data

Jul. 7, 1999  [JP]  Japan .................................. 11-192958

[51] Int. Cl.[7] ...................................................... G06K 9/00
[52] U.S. Cl. .............................................................. 382/118
[58] Field of Search ..................................... 351/204, 208; 382/118, 117, 171, 173; 348/77; 340/573

[56]            References Cited

U.S. PATENT DOCUMENTS 5,008,946  4/1991  Ando ........................................ 382/104
5,801,763  4/1991  Suzuki ....................................... 348/77
5,859,921  1/1999  Suzuki ...................................... 382/118

FOREIGN PATENT DOCUMENTS 8-175218  7/1996  Japan .

*Primary Examiner*—George Manuel
*Attorney, Agent, or Firm*—Sughrue, Mion, Zinn, Macpeak & Seas, PLLC

[57]            ABSTRACT

A face image processing apparatus is capable of extracting images of nostrils and eyes accurately and at high speed without being influenced by accessory information by employing one or a plurality of two-dimensional templates each of which expresses exactly the features of the nostrils and the eyes though the amount of information thereof is small. The face image processing apparatus includes: a face image inputting element for inputting a face image; an eye area setting element for estimating an area, in which an eye candidate is present, from the inputted face image; an eye candidate extracting element for converting the eye candidate into the data having a plurality of luminance values within the eye area; and an eye deciding element for deciding eyes within the extracted candidates and their positions.

10 Claims, 26 Drawing Sheets

FIG. 5(a)
FIG. 5(b)
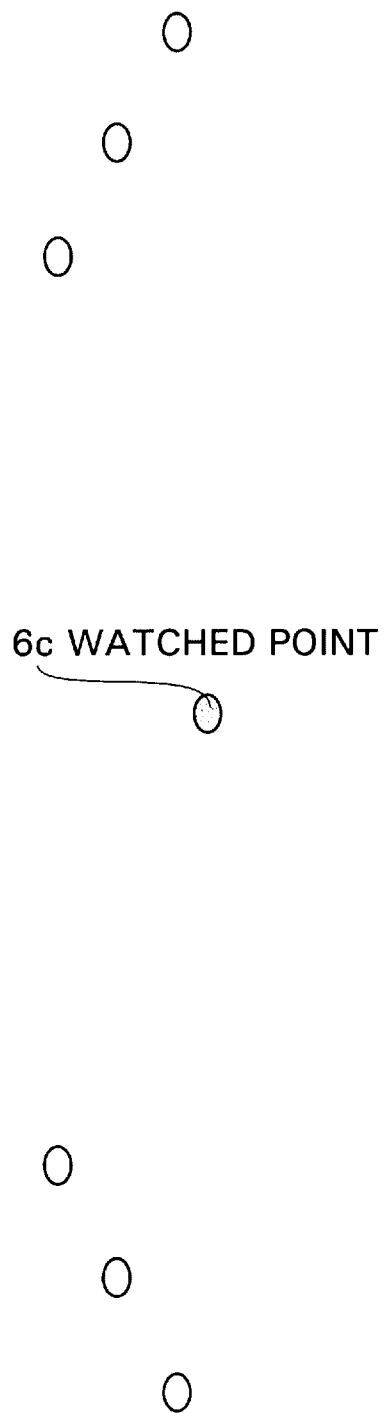
6c WATCHED POINT
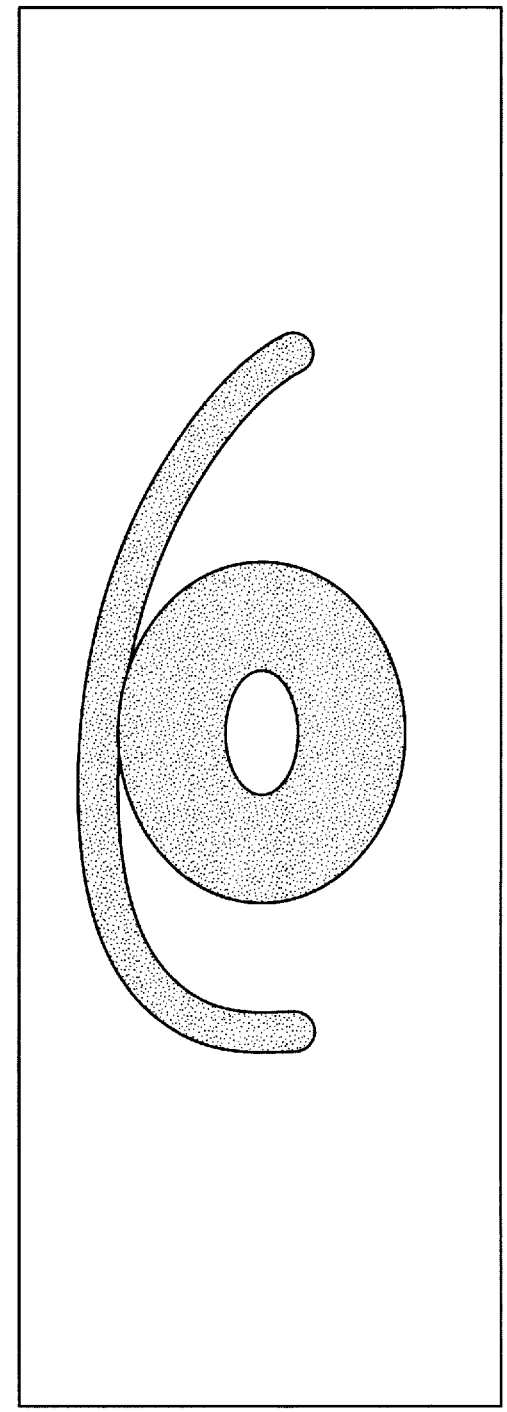

CENTER OF GRAVITY

EYE

- TEMPLATE
- NOSTRIL AREA
- WATCHED PIXEL
- PERIPHERAL PIXEL

- TEMPLATE
- EYE AREA
- WATCHED PIXEL
- PERIPHERAL PIXEL

▨ LUMINANCE VALUE 1
▦ LUMINANCE VALUE 2

FACE IMAGE PROCESSING APPARATUS EMPLOYING TWO-DIMENSIONAL TEMPLATE

BACKGROUND OF THE INVENTION

1. Field of the Invention

The present invention relates to a face image processing apparatus for extracting information related to nostrils and eyes more accurately from an input face image using a two-dimensional template.

2. Description of the Related Art

As for a conventional face image processing apparatus employing templates of drivers, there is known the apparatus disclosed in Japanese Patent Application Laid-open No. Hei 8-175218 for example. The overall configuration of the conventional apparatus is shown in the form of a block diagram in FIG. 24. This conventional face image processing apparatus includes: a camera 12 for photographing a driver; an image processing unit 13 including an A/D converter, a normalization circuit and a correlation computing circuit; a memory 16 for storing previously therein a standard template and face element arranging data related to eyebrows, eyes and the like; and an electronic control unit (ECU) 14 for discriminating a driving state of a driver on the basis of the processing results from the image processing unit 13 to output a control signal to a warning device 15 to issue a warning.

In addition, the operation, i.e., the flow of the processing, of this apparatus is shown in FIG. 26. In the figure, in Step S101, a face image of a driver is photographed, and for the resultant face image, in Step S102, the variable density normalization is carried out in which the maximum luminance is 256, and the minimum luminance is 1. After having executed the normalization processing, in Step S103, an object template is detected using a standard template. That is, for the image which has been obtained by photographing the face of a driver, a correlation operation is carried out using the standard template which is previously set, and the object template for the driver is produced by a template producing means M2. The operation or function of the template producing means M2 is carried out in a software manner by executing a control program by means of the ECU 14.

The template producing means M2 includes: an object face area setting means M5 for setting an object face area of a driver within an image which has been obtained by photographing the face of a driver; an object eye vicinity area setting means M6 for setting an object eye vicinity area, which is elongated in the vertical direction, of a face containing one eye and one eyebrow within the object face area; and an object eye area setting means M7 for setting an object eye area containing an image of an eye within the object eye vicinity area. The object face area, the object eye vicinity area and the object eye area are made object templates, respectively. After having detected the object templates, the face image of the driver is photographed again and then in Step S104, the variable density normalization is carried out. Then, for the normalized face image, in Step S105, the eye area is detected on the basis of a correlation operation utilizing the object templates. In Step S106, the ECU 14 judges the state of the eyes of the driver on the basis of the image of the eye area the information of which is successively inputted thereto. Then, if it is judged in Step S107 that the eye state of the driver has abnormality, then it is judged that the driver takes a nap, and the warning device is actuated to give a warning against his nap in Step S108.

However, if the image is processed with the image kept as the multi-valued data, then it takes a lot of time to process the data. In addition thereto, the state of the face of a person (e.g., the relation between the eyebrows and the eyes) is changed and unstable due to the accessory information such as wearing or taking-off of glasses, the weather or the hair of the head. In the conventional face image processing apparatus as described above, however, the correlation operation is carried out using the templates having a large amount of information containing eyebrows and eyes. Therefore, it takes much time to retrieve all of the input images and also the retrieval is started using the standard template having no personal information. As a result, there is the possibility that for a face image under the influence of the accessory information that is different from the normal case, the images of the nostrils and the eyes may not be detected in some cases.

SUMMARY OF THE INVENTION

In the light of the foregoing, the present invention was made in order to solve the above-mentioned problems associated with the prior art, and it is therefore an object of the present invention to provide a face image processing apparatus which is capable of extracting the images of nostrils and eyes accurately and at high speed without being influenced by the accessory information by employing one or a plurality of two-dimensional templates each of which expresses exactly the features of the nostrils and the eyes though the amount of information thereof is small.

According to one aspect of the present invention, there is provided a face image processing apparatus including: face image inputting means for inputting a face image; eye area setting means for estimating an area, in which an eye candidate is present, from the inputted face image; eye candidate extracting means for converting the eye candidate into the data having a plurality of luminance values within the eye area; and eye deciding means for deciding eyes within the extracted candidates and their positions.

According to another aspect of the present invention, there is provided a face image processing apparatus including: face image inputting means for inputting a face image; nostril area setting means for estimating an area, in which a nostril candidate is present, from the inputted face image; nostril candidate extracting means for converting the nostril candidate into the data having a plurality of luminance values within the nostril area; nostril deciding means for deciding nostrils within the extracted nostril candidate; eye area setting means for estimating an area, in which an eye candidate is present, from the decided nostrils; eye candidate extracting means for converting the eye candidate into the data having a plurality of luminance values within the eye area; and eye deciding means for deciding the eyes within the candidate which has been extracted by the eye candidate extracting means and their positions.

In a preferred form of the invention, it is characterized in that either the nostril candidate extracting means or the eye candidate extracting means carries out the simple matching in relative luminance between a watched pixel and its peripheral pixels using a two-dimensional template and at least one threshold which are previously set.

In another preferred form of the invention, it is characterized in that either the nostril candidate extracting means or the eye candidate extracting means limits an object, for which the matching is carried out, further using a variable extraction luminance threshold.

In a further preferred form of the invention, it is characterized in that either the nostril candidate extracting means or the eye candidate extracting means employs a plurality of variable extraction luminance thresholds or two-dimensional templates.

In a yet further preferred form of the invention, it is characterized in that either the nostril candidate extracting means or the eye candidate extracting means relaxes the two-dimensional template in accordance with the degree of the image extraction.

BRIEF DESCRIPTION OF THE DRAWINGS

The above and other objects as well as advantages of the present invention will become clear by the following description of the preferred embodiments of the present invention with reference to the accompanying drawings, wherein:

FIGS. 5(a) and 5(b) are diagrams showing a template of the eye extracting means and an eye candidate, respectively, in the present invention;

DETAILED DESCRIPTION OF THE PREFERRED EMBODIMENTS

The preferred embodiments of the present invention will hereinafter be described in detail with reference to the accompanying drawings.

(First Embodiment)

Figure 1:
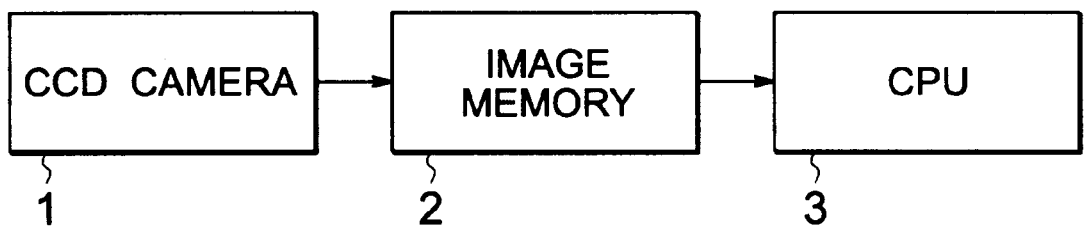
FIG. 1 is a block diagram showing a schematic configuration of a face image processing apparatus according to a first embodiment of the present invention.

FIG. 1 is a block diagram showing a schematic configuration of a face image processing apparatus according to a first embodiment of the present invention. The face image processing apparatus according to the present embodiment includes: a CCD camera 1 for photographing a face image; an image memory 2 for storing therein image data of the face image which has been outputted from the CCD camera 1; and a CPU 3 for reading out the image data from the image memory 2 to execute the image processing on the basis of the image data thus read out.

Figure 2:
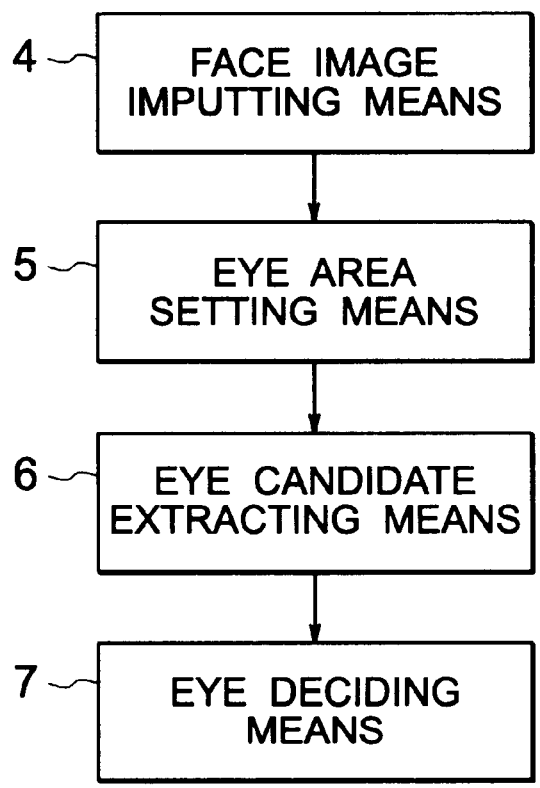
FIG. 2 is a block diagram for explaining a functional configuration of the face image processing apparatus according to the first embodiment.

FIG. 2 is a functional block diagram showing the outline of the processing in the CPU 3 shown in FIG. 1. In the figure, the CPU 3 includes: face image inputting means 4 for reading out the image data from the image memory 2 to input thereto the image data thus read out; eye area setting means 5 for setting an eye area on the basis of the image data which has been inputted to the face image inputting means 4; eye candidate extracting means 6 for extracting an eye candidate on the basis of the output from the eye area setting means 5; and eye deciding means 7 for deciding the images of eyes and their positions where the images of the eyes are located on the basis of the output of the eye candidate extracting means 6. The operations or functions of these means functionally illustrate the contents of operation or processing of the CPU 3 which are carried out in a software manner by executing a program by means of the CPU 3.

First of all, the CPU 3 reads out the image data of the face image from the image memory 2 to input the image data thus read out to the face image inputting means 4. An area in which the images of eyes appear to be present within the input image is estimated by the eye area setting means 5 and subjected to a luminance conversion by the eye candidate extracting means 6 to extract an eye candidate. In this connection, the data that has been obtained by the luminance conversion is stored in a memory which is different from the image memory 2 in which the input image is stored in such a way that the input image data can also be referred later. In addition, the eye candidate and the eye positions are decided from the extracted area by the eye deciding means 7. Those means will be described hereinbelow in detail.

Figure 3:
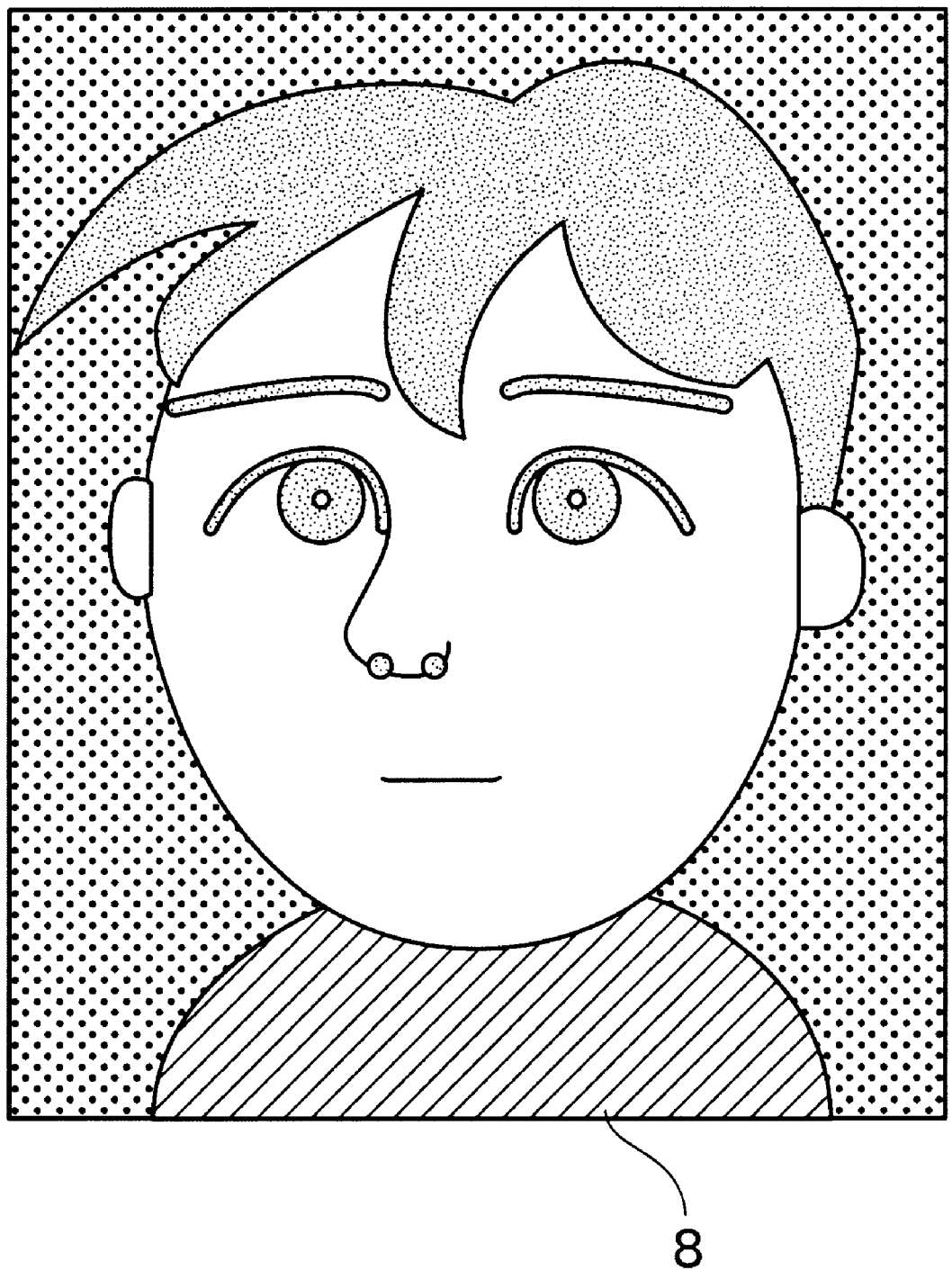
FIG. 3 is a diagram showing an input image from a camera in the present invention.
Figure 8A:
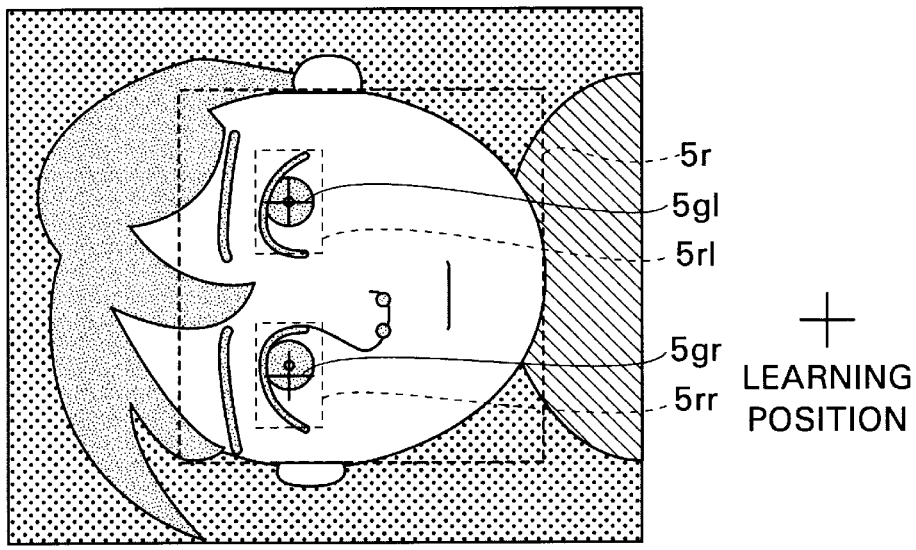
FIGS. 8(a) and 8(b) are diagrams for explaining an eye area setting means in the present invention.
Figure 8B:
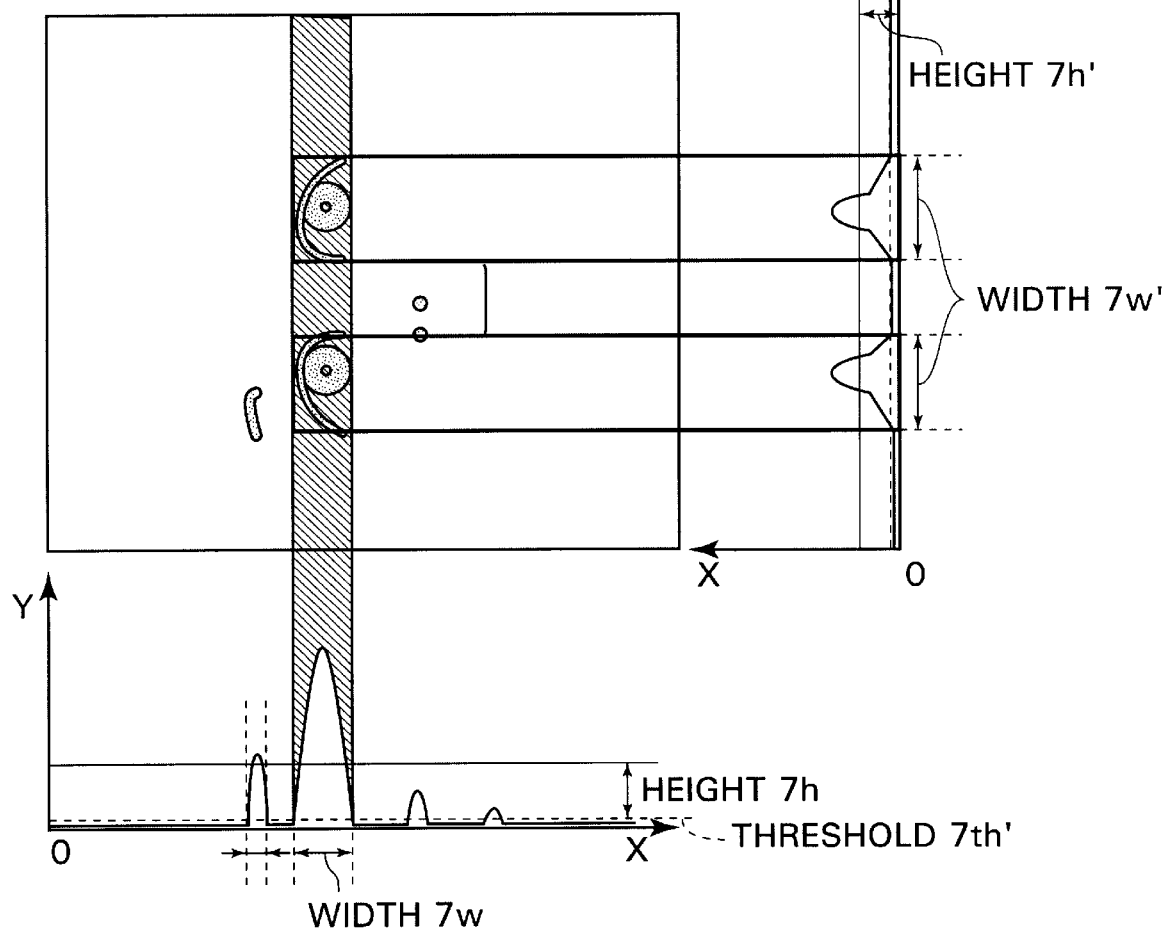

FIG. 3 is a diagram showing a face image 8 that is obtained by photographing a person by the CCD camera 1. In the eye area setting means 5 for estimating an area in which an eye candidate appears to be present within the input image, for example, a relatively large rectangular eye retrieving area Sr, which covers the whole face, as shown in FIG. 8 is set during the eye retrieving mode, while a relatively small rectangular eye tracking areas 5rl and 5rr each of which covers only an eye are set during the eye tracking mode. By the eye retrieving mode is meant the state in which the eye position learning is not yet carried out (the eye is not yet found out), while by the eye tracking mode is meant the state in which the eye position learning has already been carried out (the eye has already been found out). The retrieval area 5r is set in such a way as to be limited to the area in which the face of a driver falls within the picture with a normal driving posture. The tracking areas 5rl and 5rr are set in such a way as to have the predetermined widths from eye learning positions (or last eye positions) 5gl and 5gra, respectively. In this case, while the eye areas are set for the both eyes, the eye area may be set for only one of right or left eye.

Figure 4:
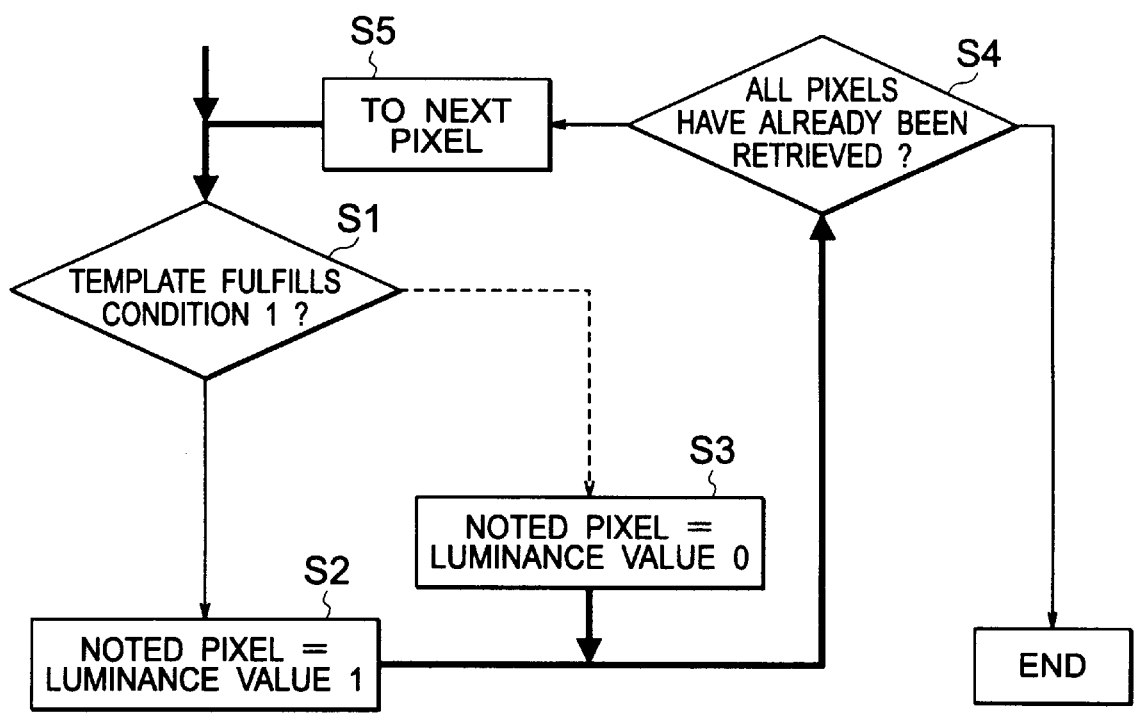
FIG. 4 is a flow chart for explaining the flow of the processing in an eye extracting means and a nostril extracting means in the first and a second embodiments of the present invention.

Next, the eye candidate extracting means 6 will hereinbelow be described. As shown in a flow chart of FIG. 4, in Step S1, the eye candidate extracting means 6 carries out a simple matching within the eye area using a two-dimensional template 6t (refer to FIG. 5(a) for example) which is previously prepared and which expresses simply and exactly the eye shape in order to extract the element which appears to be the eye candidate (refer to FIG. 5(b)). In the eye candidate extracting means 6, a watched pixel 6c is successively moved in the X and Y directions within the area which is set by the eye area setting means 5 to confirm the condition of an eye judgement element pixel (=a point indicated by the two-dimensional template) of the peripheral pixels of the watched pixel 6c, thereby judging whether or not the watched pixel 6c is an eye candidate pixel.

The criterion is a condition A (for the watched pixel, each of all of the luminance values of the eye judgement element pixels is equal to or larger than a predetermined threshold 6th).

Figure 6A:
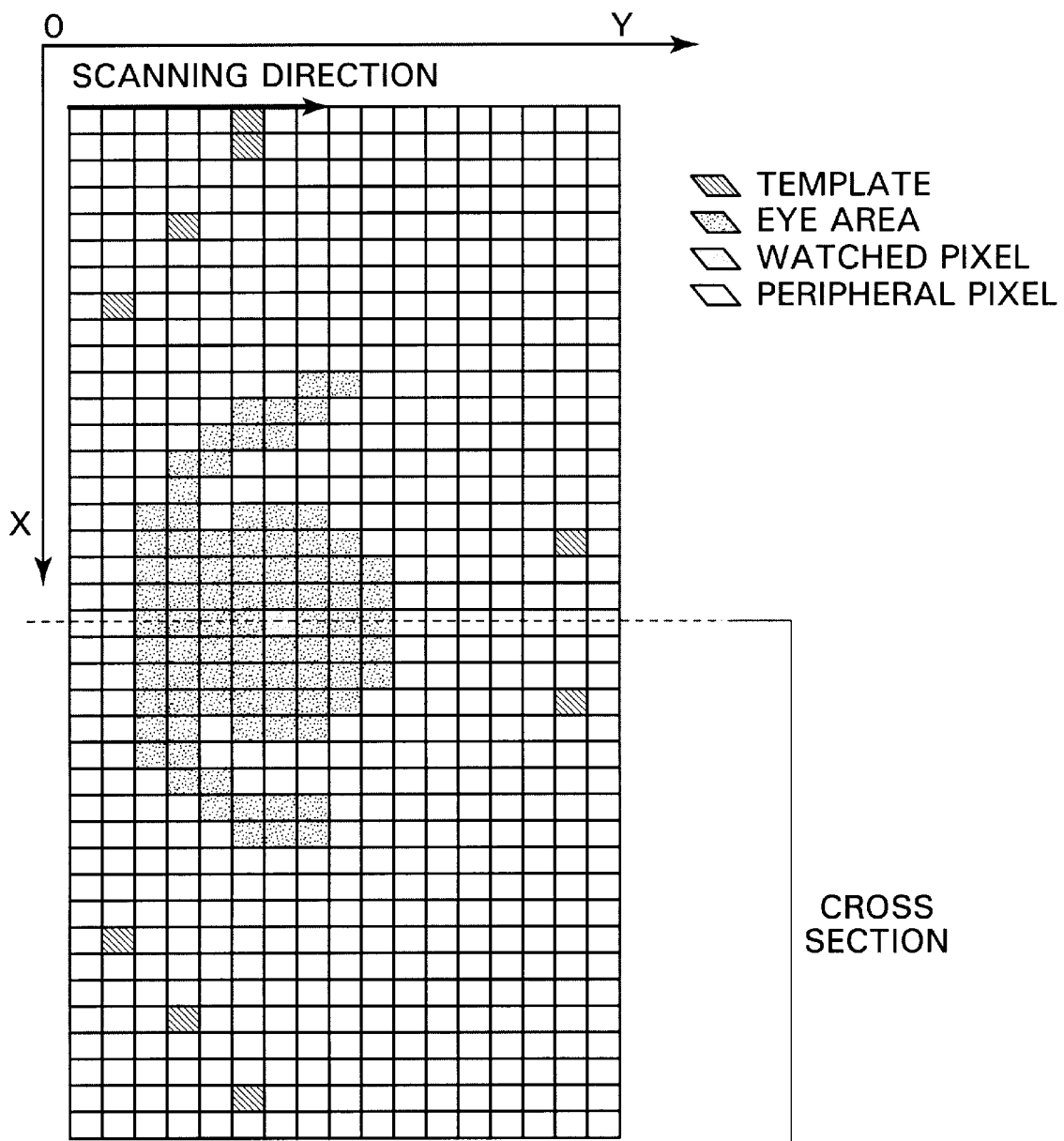
FIGS. 6(a) and 6(b) are diagrams for explaining the operation of the eye extracting means.
Figure 6B:
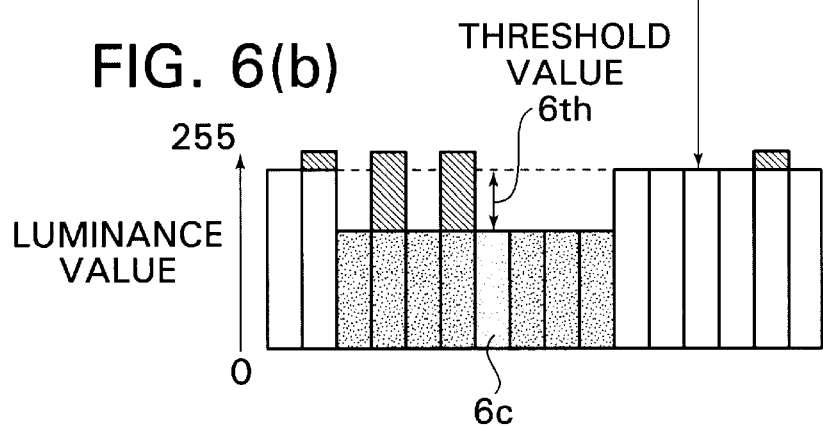

For the luminance value of the watched point (the meshed pixel) shown in FIG. 6, if each of all of the luminance values of the eye judgement element pixels (the white pixels) is equal to or larger than +6th ("YES" in FIG. 4 indicated by the solid line), then it is judged that the watched point is the eye candidate pixel (shown in a cross sectional view of FIG. 6(b)).

Figure 7A:
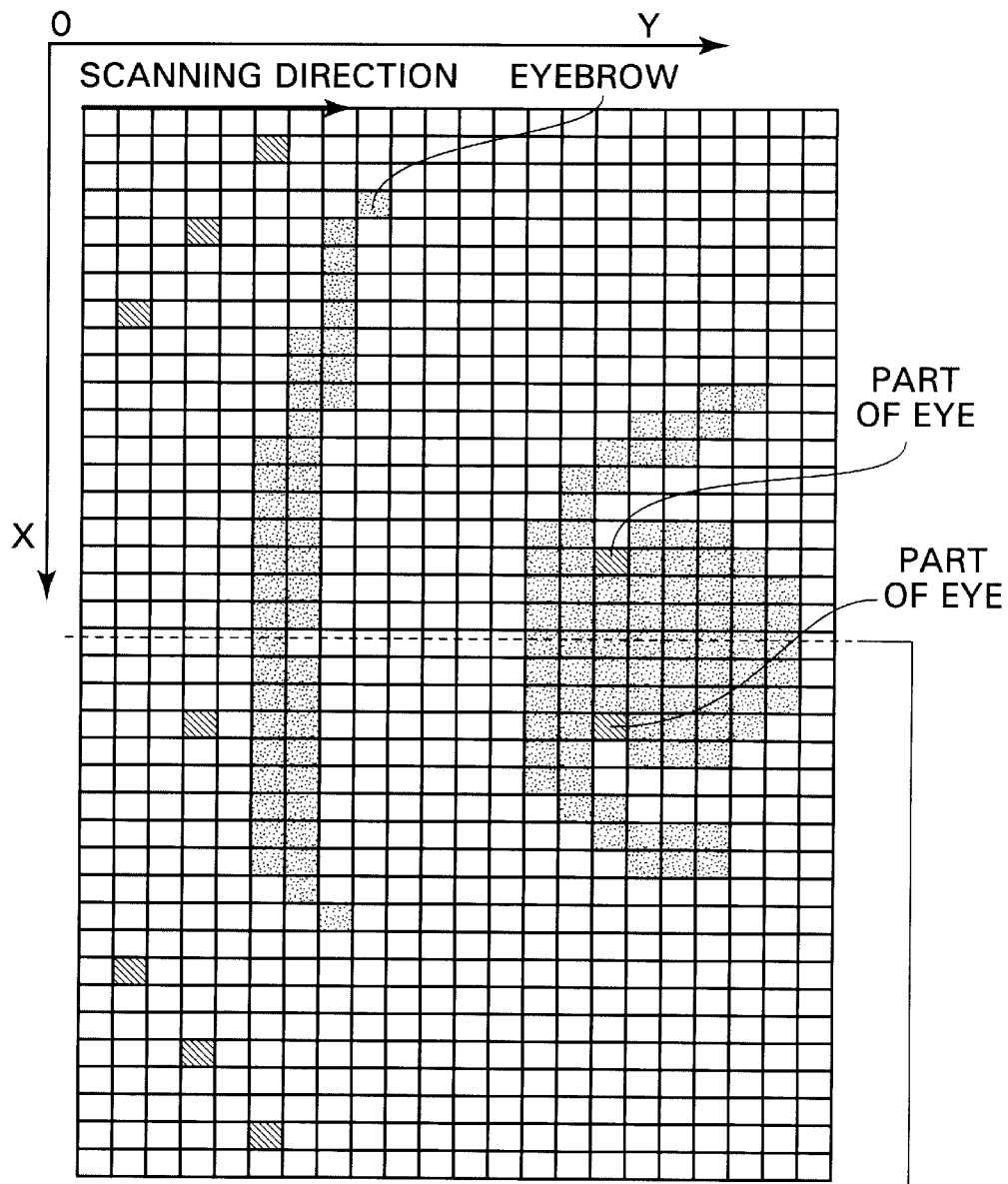
FIGS. 7(a) and 7(b) are diagrams showing the situation when selecting an eyebrow by the eye extracting means.
Figure 7B:
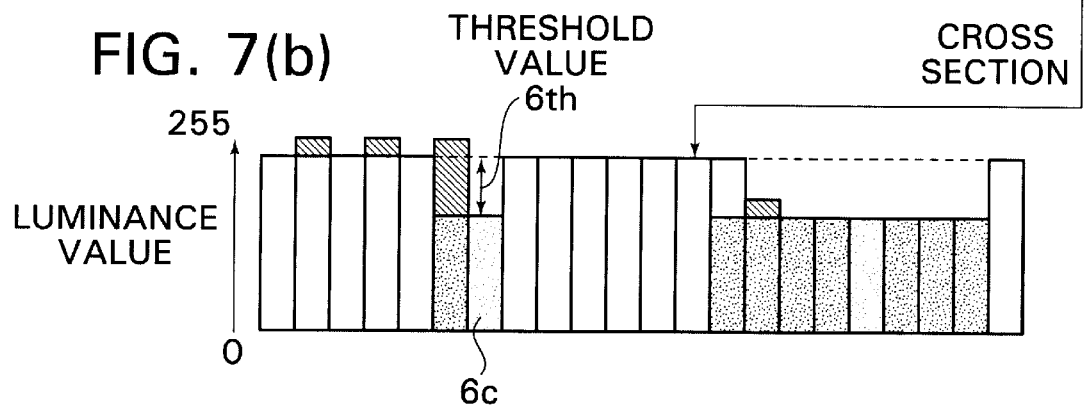

Then, in Step S2, the luminance value of the pixel of the watched point, i.e., the watched pixel is set to 1. On the other hand, if the judgement result in Step S1 is "NO" (indicated by the broken line in FIG. 4)(if all of the luminance values of the eye judgement element pixel are each equal to or smaller than +6th), then in Step S3, the luminance value of the watched pixel is set to 0. Next, in Step S4, it is judged whether or not the retrieval has already been completed for all the pixels. If it is judged in Step S4 that the retrieval is not yet completed for all of the pixels ("NO"), then the processing target is changed over to the next pixel. On the other hand, if it is judged in Step S4 that the retrieval has already been completed for all of the pixels ("YES") (indicated by the solid line), then the processing is completed (in FIG. 6, the pixels drawn with the slanting lines= the peripheral pixels, and the black pixels=the eye candidate pixels). In this connection, the reason that the image of the eye can be readily extracted, while the image of the eyebrow is hardly extracted is that as shown in FIGS. 7(a) and 7(b), the hair of a head is present in the upper position with respect to the eyebrows and eyes are present in the lower position with respect to the eyebrows and hence when employing the two-dimensional template having the eye shape, it is difficult for the eyebrows to fulfill all of the whole condition A due to the shape of the eyebrows.

Figure 9:
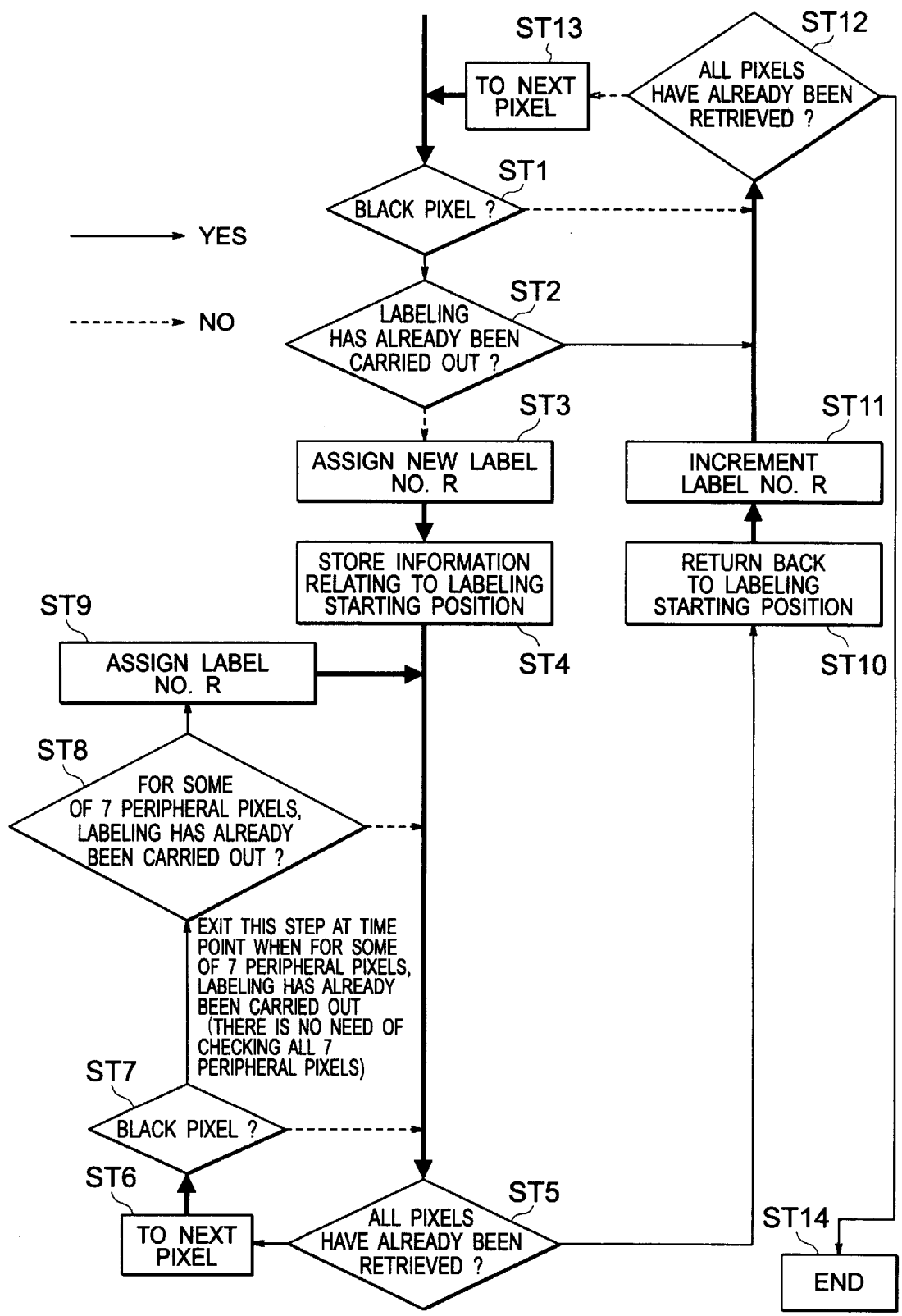
FIG. 9(a) is a flow chart for explaining the flow of the labeling in an eye deciding means of the present invention.
FIG. 9(b) is a flow chart for explaining the flow of labeling in eye deciding means of the prior art.
Figure 9:
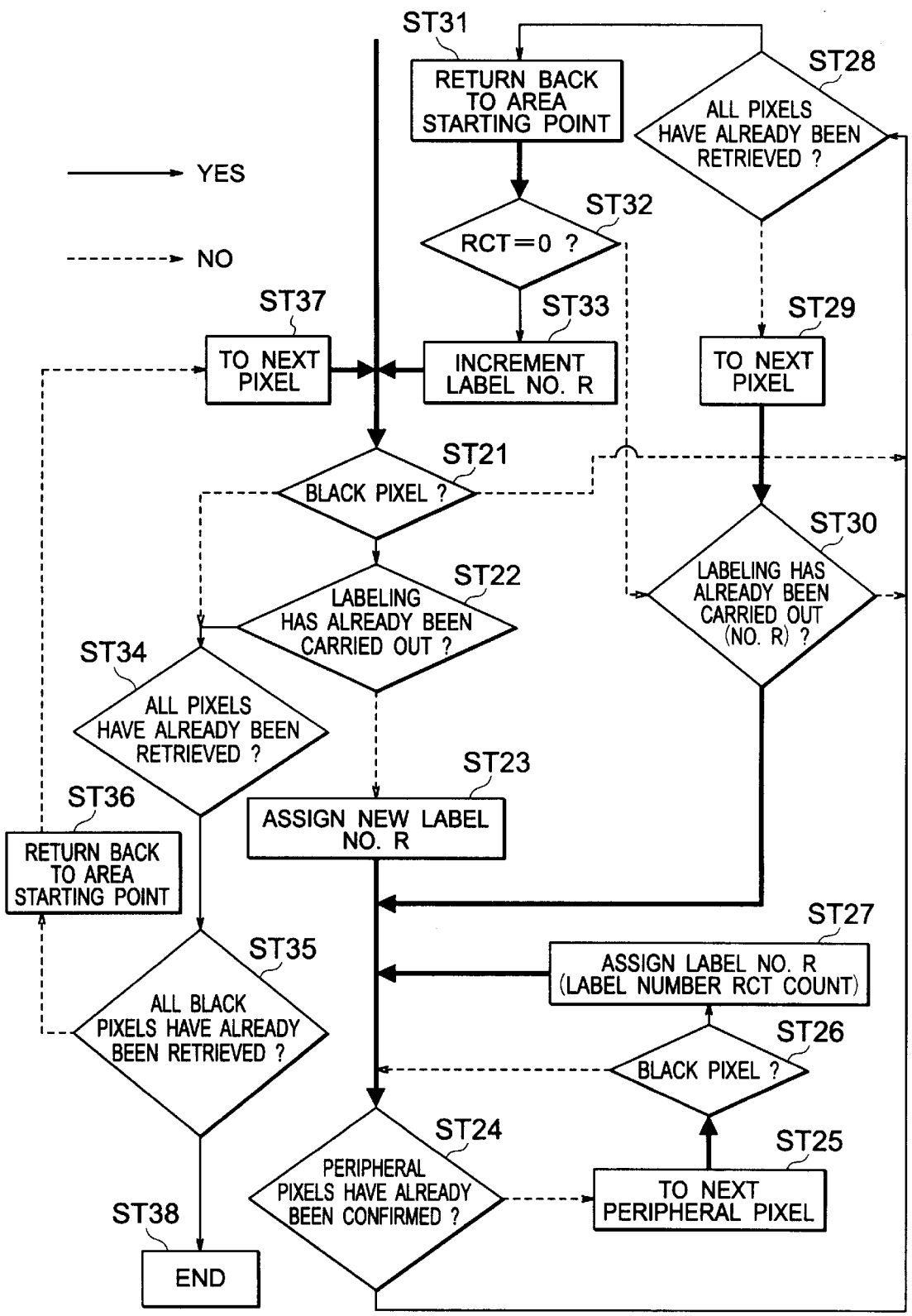

Next, the eye candidate in the area which has been extracted in the above-mentioned processing and the eye positions are decided by the eye deciding means 7. For the area which has been extracted by the eye candidate extracting means 6, as shown in of FIG. 8(b), with respect to each of the X coordinates, the number of black pixels which are present on the Y-axis is counted and then the resultant numerical value is projected on the X-axis in order to obtain the intensity distribution. Then, the area which has a predetermined width 7w and a predetermined length 7h is recognized as the strip area, and also with respect to each of the Y coordinates within the strip area thus recognized, the number of black pixels which are present on the Y-axis is counted and then the resultant numeric value is projected on the Y-axis in order to obtain the intensity distribution. Then, the area which has a predetermined width 7w' and a predetermined length 7h' is made the eye candidate area. After having estimated the eye candidate area, the labeling is carried out to decide the eye candidate. But, in the normal (conventional) labeling, as shown in of FIG. 10(b), since the labeling for the eight directions for each pixel needs to be confirmed and also the loop until for all of the pixels, the labeling has been completed is required, it takes a lot of time. Then, as shown in FIG. 10(a), the labeling is simply carried out by limiting the required processing to the confirmation of the labeling with respect to the seven directions and one loop processing. FIGS. 9(a) and 9(b) illustrate the flow charts of labeling in the present invention and the prior art. FIG. 9(a) shows the flow of the labeling processing of the present invention, whereas FIG. 9(b) shows the flow of the normal (conventional) labeling processing.

Next, the description will hereinbelow be given with respect to the labeling processing according to the present invention while referring to the flow chart of FIG. 9(a).

(1) For a predetermined area of an image for which the binary processing has been carried out, for example, the watched pixel is successively moved from the upper left-hand portion of the area to judge first whether or not the watched pixel is the black pixel (Step ST1). If it is judged in Step ST1 that the watched pixel is the black pixel, then it is judged whether or not the labeling has already been carried out therefor (Step ST2). If it is judged in Step ST2 that the labeling has not yet been completed therefor, then a new label number (NO. R) is assigned thereto (Step ST3).

(2) Thereafter, the information related to the position where the labeling is started (=the current position) is stored (Step ST4), and then as shown in FIG. 10(a), the pixels are successively scanned in the scanning direction from the position where the labeling is started. That is, it is judged whether or not all of the pixels have already been retrieved (Step ST5). If it is judged in Step ST5 that all of the pixels have not yet been retrieved, then the processing target is changed over to the next pixel (Step ST6) to judge whether or not the pixel of interest is the black pixel (Step ST7). During the scanning, the labeling states of the seven peripheral pixels of the watched pixel are judged. If it is judged in Step ST7 that the watched pixel is the black pixel ("YES") and also it is judged in Step ST8 that for some of the seven peripheral pixels, the labeling has already been carried out ("YES"), then the label number (NO. R) is assigned to the watched pixel (Step ST9)(At this time, the new label number (NO) is not provided). In any of the cases other than that case, no label is assigned. That is, if for one pixel of the seven peripheral pixels, the labeling has already been carried out, then the label is assigned to the watched pixel at this time point, and the processing target is changed over to the next pixel.

(3) If the processing proceeds to the retrieval area end (i.e., if it is judged in Step ST5 that all of the pixels have been retrieved ("YES")), then the processing proceeds to the labeling starting position (Step ST10). Then, the label number (NO. R) is incremented (Step ST11). Then, it is judged whether or not all of the pixels have already been retrieved (Step ST12). If it is judged in Step ST12 that all of the pixels have not yet been retrieved ("NO"), then the processing target is changed over to the next pixel (Step ST13), and thereafter, the processing proceeds to Step ST11 in order to repeatedly carry out the above-mentioned scanning.

(4) If it is judged in Step ST12 that for all of the points within the retrieval area, the scanning (1) to (3) has been completed ("YES"), then the processing is completed (Step ST14).

On the other hand, the normal (i.e., the conventionally known) operation is as shown in the flow chart of FIG. 9(b).

(A) For a predetermined area of the image after completion of the binary operation, for example, the watched pixel is successively moved from the higher left-hand portion to judge first whether or not the watched pixel is the black pixel (Step ST21). If it is judged in Step ST21 that the watched pixel is the black pixel, then it is judged whether or not the labeling has already been completed therefor (Step ST22). If it is judged in Step ST22 that the labeling has not yet been carried out therefor, then the new label number (NO. R) is assigned thereto (Step ST23). If it is judged in Step ST21 that the watched pixel is not the black pixel or it is judged in Step ST22 that the labeling has already been carried out, then it is judged whether or not all of the pixels have been retrieved (Step ST34). Then, it is judged whether or not for all of the black pixels, the labeling has already been carried out (Step ST35). If it is judged in Step ST 34 that all of the pixels have already been retrieved, or it is judged in Step ST35 that for all of the pixels, the labeling has not yet been carried out, then the processing target is changed over to the next pixel (Step ST37), and then the processing proceeds to Step ST21 again.

Figure 10:
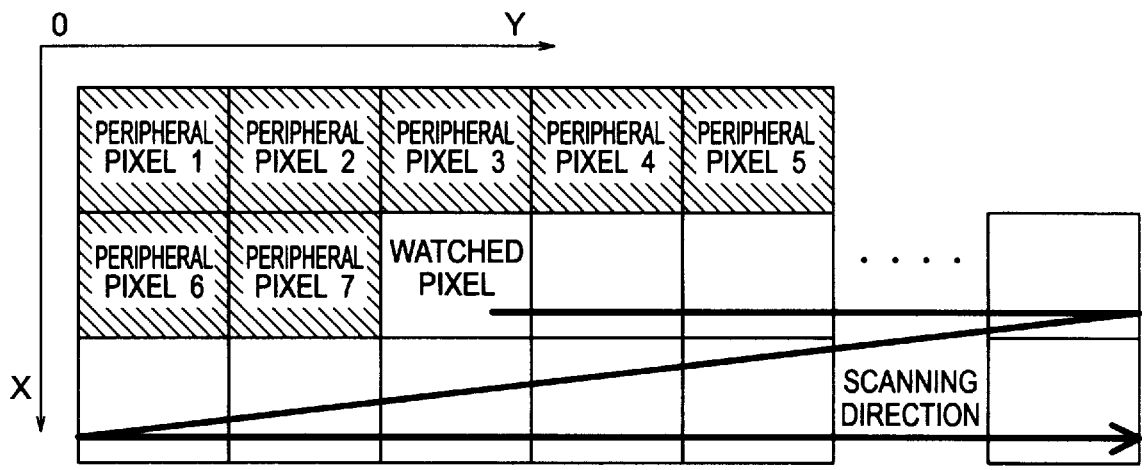
FIG. 10(a) is a diagram for explaining the scanning direction in labeling in the present invention.
FIG. 10(b) is a diagram for explaining the scanning direction in labeling in the prior art.
Figure 10:
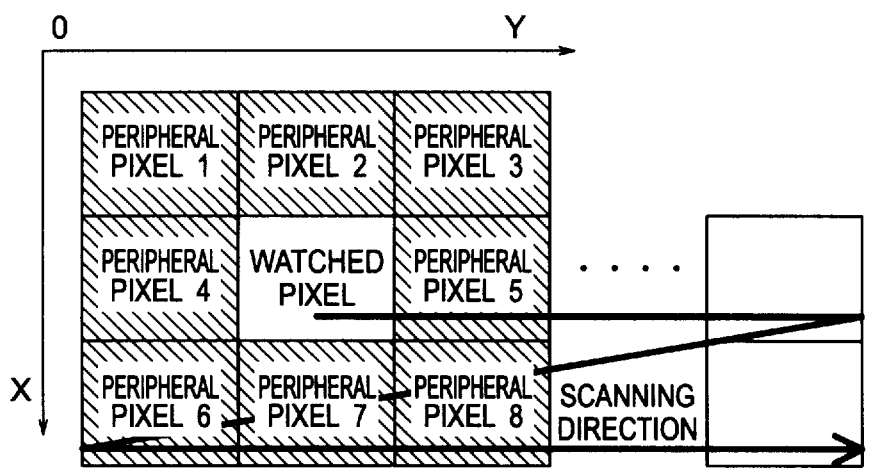

(B) After completion of the processing in Step ST23, as shown in a part (b) of FIG. 10, the eight peripheral pixels of the watched pixel are confirmed (Step ST24). If the labeling has not yet been carried out, then the processing target is changed over to the next peripheral pixel (Step ST25). Then, it is judged whether or not the pixel of interest is the black pixel (Step ST26). If it is judged in Step ST26 that the pixel of interest is the black pixel, then the same label number (NO.R) as that of the watched pixel is assigned to each of the peripheral pixels to count the label number RCT (Step ST27).

(C) Next, the processings (B)(Steps ST24 to ST27) are successively executed in the scanning direction. If it is judged in Step ST24 that for all of the eight peripheral pixels, the labeling has already been carried out, then it is judged whether or not all of the pixels have already been retrieved (Step ST28). If this judgement result is NO, then the processing target is changed over to the next pixel (Step ST29), and then it is judged whether or not the labeling has already been carried out (Step ST30). If it is judged in Step ST30 that the labeling has already been carried out, then the processing proceeds to Step ST24. On the other hand, if it is judged in Step ST30 that the labeling has not yet been carried out, then the processing proceeds to Step ST28. In such a way, the above-mentioned scanning operation is repeatedly carried out until the labeling has been carried out for all of the desired pixels.

(D) In such a way, if the operation up to (C) has been completed, i.e., it is judged in Step ST28 that all of the pixels have already been retrieved, then the processing is returned back to the area starting position (Step ST31). Then, it is judged whether or not the label number RCT count is zero (Step ST32). If it is judged in Step ST32 that the label number RCT count is not zero, then the processing proceeds to Step ST30. On the other hand, if it is judged in Step ST32 that the label number RCT count is zero, then the label number (NO. R) is incremented (Step ST33), and the processings (A) to (C) are repeatedly executed.

(E) If for all of the black pixels within the retrieval area, the scanning of the processings (A) to (D) has already been completed, i.e., it is judged in Step ST35 that all of the black pixels have already been retrieved, then the processing is completed (Step ST38).

Figure 11A:
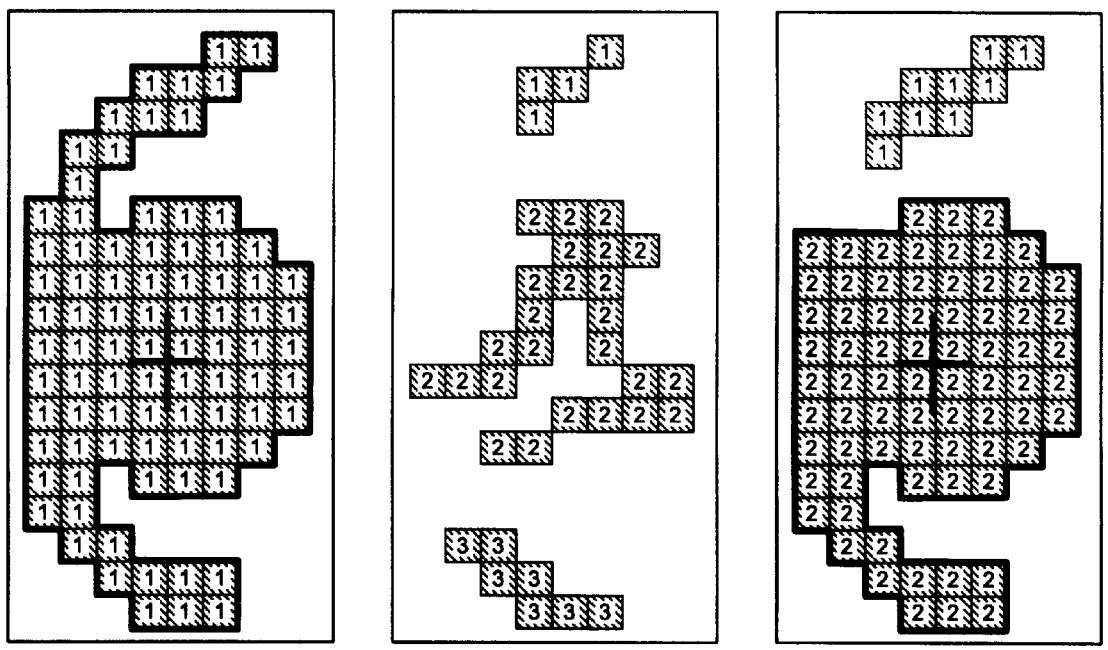
FIGS. 11(a) through 11(c) are diagrams for explaining the different states of the labeling of three examples, respectively.
Figure 11B:
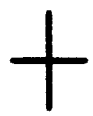
Figure 11C:

In addition, in the above-mentioned labeling processing, the position of the center of gravity in each of the X and Y directions is calculated during the labeling to be made the eye position. But, when the image of interest can not be judged as the image of the eye on the basis of the widths and the areas of the labeled candidate in the X and Y directions, it is judged that the eye has not yet been detected. Or, when there are two or more elements, one candidate which is most apparently the image of the eye is extracted on the basis of the widths and the areas of the elements in the X and Y directions, and then the center of gravity thereof is made the eye position. Such three examples are shown in FIGS. 11(a) to 11(c), respectively. FIG. 11(a) shows the case where the image of the eye is expressed in the form of one continuous area and in the eye area, "1s" are continuously labeled on the pixels. FIG. 11(b) shows the case where the image of the eye is divided into several parts due to the reflection or the like. In this example, "1s", "2s" and "3s" are respectively labeled on three areas which are obtained by dividing the continuous area thereinto. In addition, FIG. 11(c) shows the case where a part of the image of the eye is divided from the main part to produce two areas and "1s" and "2s" are respectively labeled on the two areas.

In each of FIGS. 11(b) and 11(c), the area on which "2s" are labeled is extracted as the eye candidate.

In addition, the information related to the eye position which is decided by the eye deciding means 7 is stored in the memory and is used to set the eye area during the eye tracking mode.

(Second Embodiment)

Figure 12:
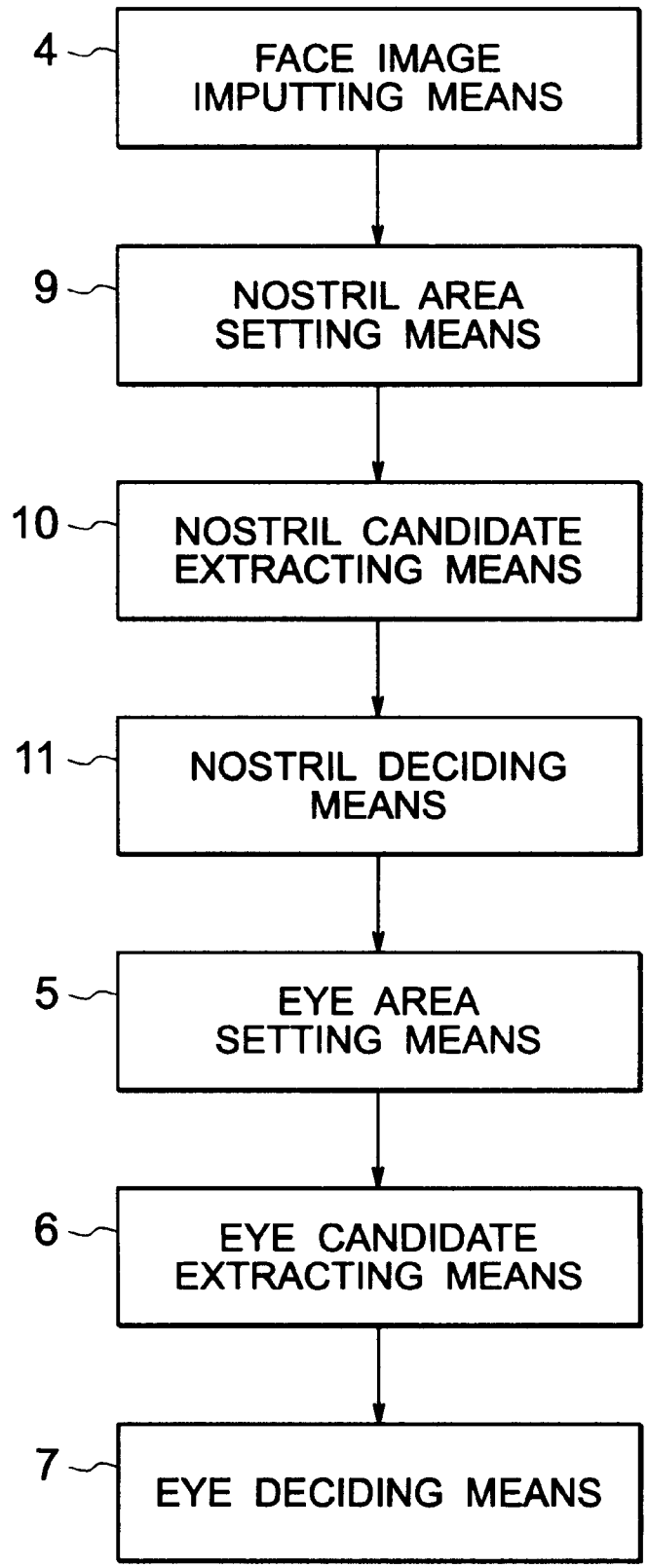
FIG. 12 is a block diagram showing a functional configuration of a face image processing apparatus according to the second embodiment of the present invention.
Figure 13:
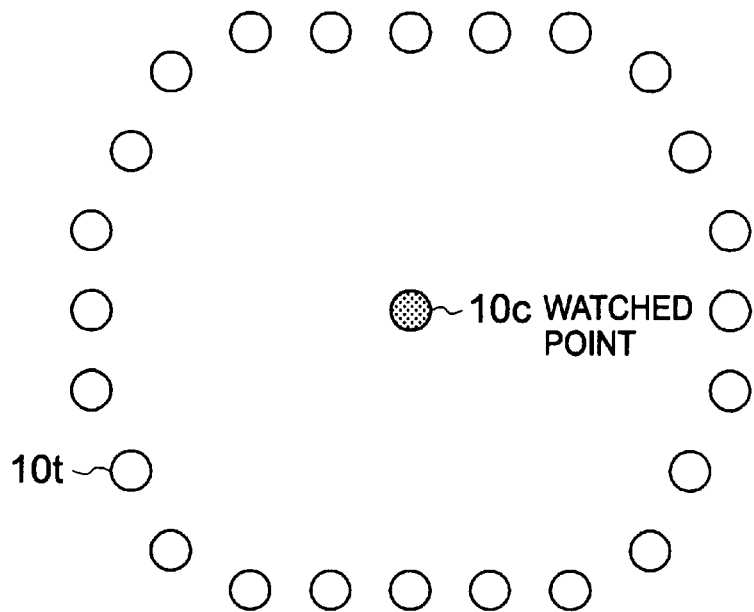
FIGS. 13(a) and 13(b) are diagrams showing a template of nostril extracting means and a nostril candidate, respectively, according to the second embodiment of the present invention.
Figure 13:
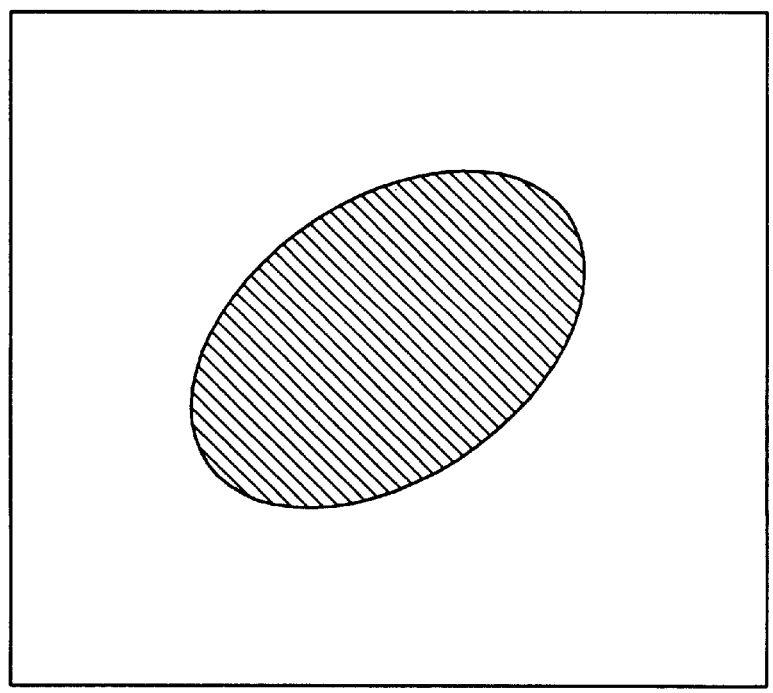

A second embodiment of the present invention is shown in FIGS. 12 to 16. In the present embodiment, as shown in FIG. 12, a nostril area setting means 9, a nostril candidate extracting means 10 and a nostril deciding means 11 are added to the above-mentioned first embodiment, and also the eye setting means 5 is changed.

First of all, the description will hereinbelow be given with respect to the nostril area setting means 9 for estimating the area in which the nostril candidate appears to be present within the input image. In the nostril area setting means 9, during the nostril retrieving mode for example, a relatively large rectangular nostril retrieving area 9r which contains therein the area extending from the eyes to the chin is set, while during the nostril tracking mode, a relatively small rectangular nostril tracking area 9rr which contains therein only the nose is set. In this connection, by the nostril retrieving mode is meant the state in which the nostril position learning is not yet completed (i.e., the state in which the nostril is not yet found out), while by the nostril tracking mode is meant the state in which the nostril learning has already been completed. The nostril retrieving area 9r is set in such a way as to be limited to the area in which the image of the face falls within the picture with the normal driving posture. In addition, for the nostril tracking area 9rr, there is set the area having a predetermined width from the nostril learning position (or, the last nostril position) 9gr.

Figure 14A:
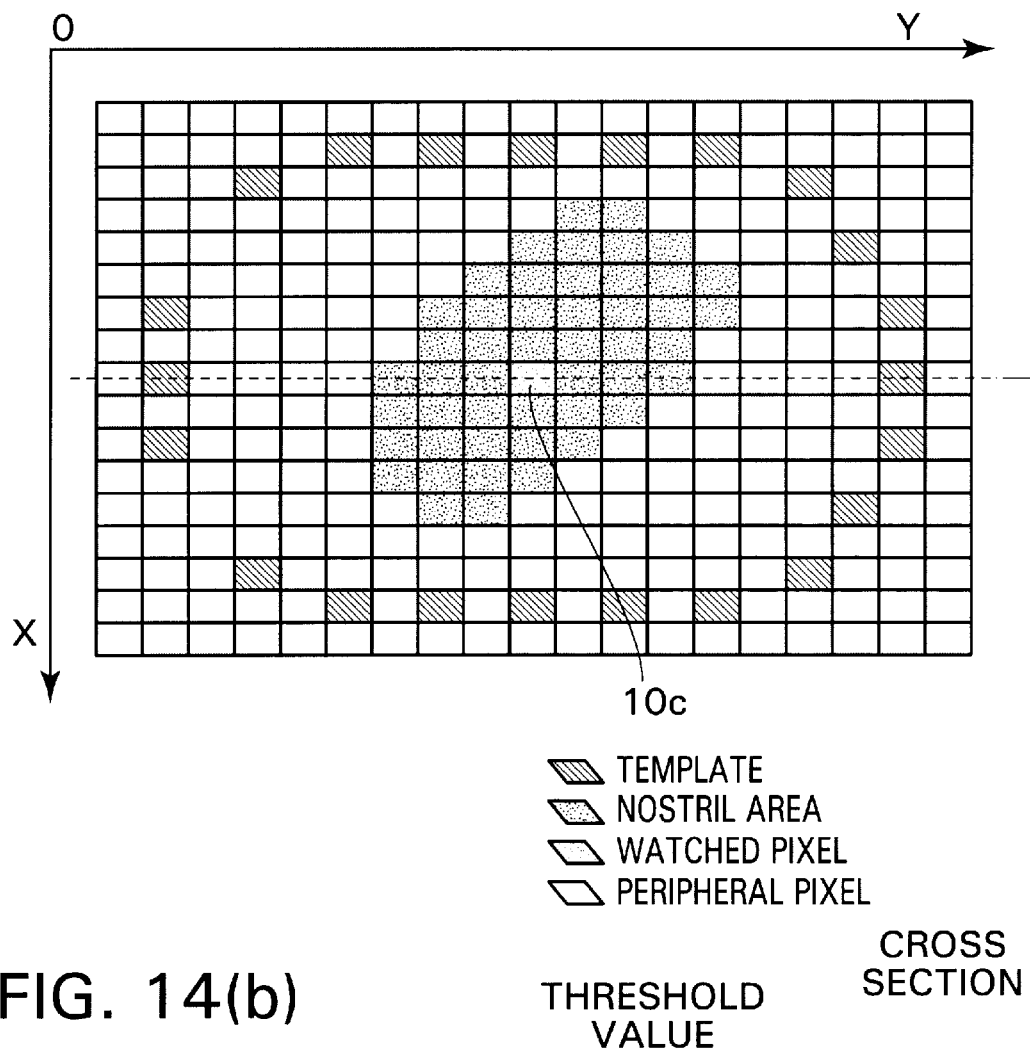
FIGS. 14(a) and 14(b) are diagrams for explaining the nostril extracting means.
Figure 14B:
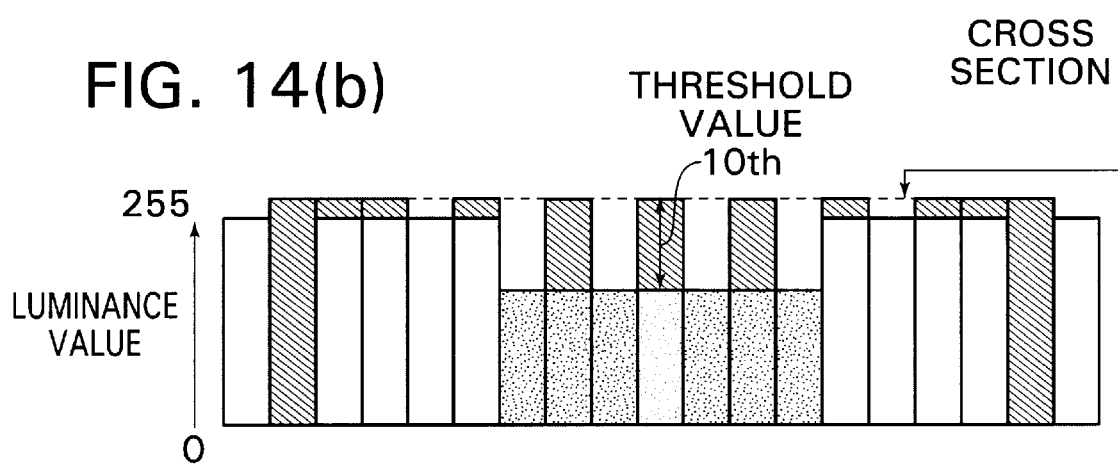
Figure 15:
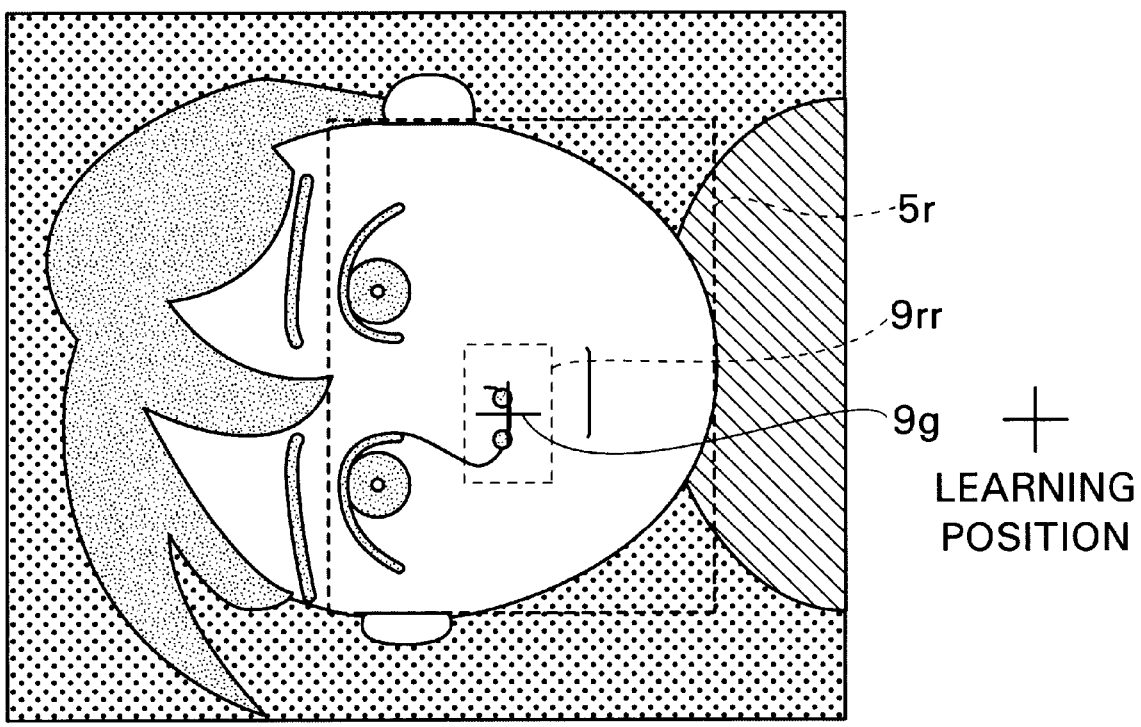
FIG. 15 is a diagram for explaining a nostril area setting means according to the second embodiment of the present invention.

The nostril candidate extracting means 10 carries out the simple matching within the nostril area using a two-dimensional template 10t as shown in FIG. 13(a) for example to extract the element which appears to be the nostril candidate as shown in FIG. 13(b). More specifically, in the nostril candidate extracting means 10, as shown in FIG. 14(a), a watched pixel 10c is successively moved in the X and Y directions within the area which is set by the nostril area setting means 9 to confirm the condition of the nostril judgement element pixels (=the points indicated by a two-dimensional template) of the peripheral pixels of the watched pixel 10c to judge whether or not the watched pixel 10c is the nostril candidate pixel. The criterion is the condition A (for the watched pixel, each of all of the luminance values of the nostril judgement element pixels is equal to or larger than a predetermined threshold 10th). As shown in FIG. 14(b) as the cross section of FIG. 14(a), if for the luminance value of the watched point (the meshed pixel) 10c, each of the luminance values of all of the nostril judgement element pixels (the white pixels) exceeds +10th, it is judged that the watched point is the nostril candidate pixel and then the processing target is changed over to the next pixel. In FIGS. 14(a) and (b), the pixel which is expressed by the slanting lines is the peripheral pixel, and the black pixel is the eye candidate pixel.

Next, the nostril candidate in the area which has been extracted in the manner as described above and its nostril position are decided by the nostril deciding means 11. The labeling is carried out for the area that has been extracted by the nostril candidate extracting means 10 to decide the nostril candidate. The labeling is carried out in the same manner as in the above-mentioned first embodiment.

Figure 16:
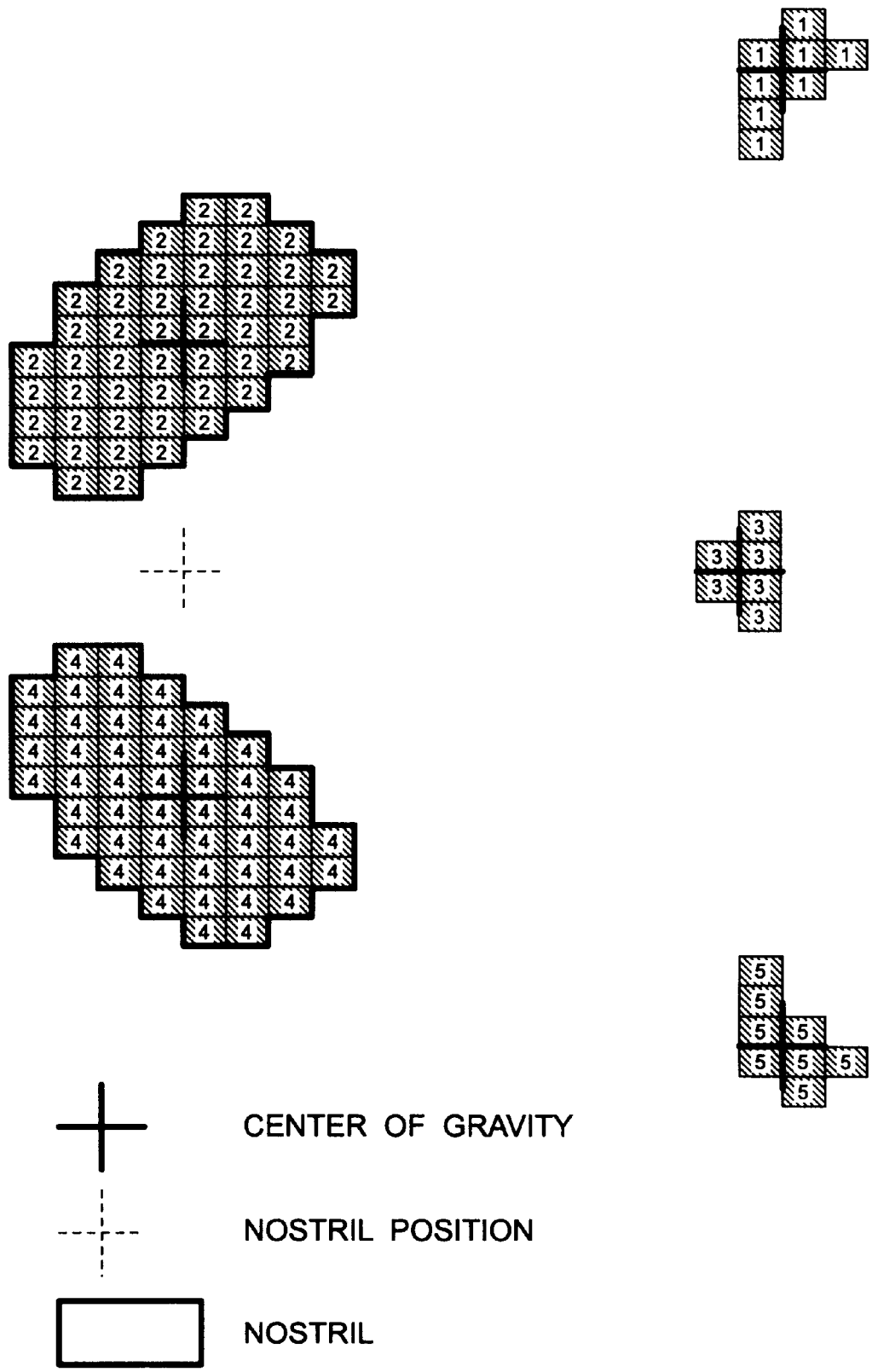
FIG. 16 is a diagram for explaining the labeling of a nostril deciding means according to the second embodiment of the present invention.

In addition, during the labeling in the above-mentioned labeling processing, the position of the center of gravity of the extracted area in each of the X and Y directions is calculated to be made the nostril candidate position. For the nostril candidates, as shown in FIG. 16, the images in which the two areas are arranged which are close in the size and the shape (close to the ellipse) in the transverse direction of the face to each other are retrieved to be made the images of the nostrils. In this connection, the nostril position is assumed to be the middle point between the two candidates. If the images of interest can be judged to be the nostrils on the basis of the widths in the X and Y directions, the areas and the like of the labeled elements, it is judged that the nostrils are not yet detected. Or, when there are two or more candidates, one pair of candidates which are most apparently the images of the nostrils from the widths in the X and Y directions and the areas of the candidates are extracted and the middle point between the centers of gravity of the one pair of candidates is made the nostril position.

The information related to the nostril position which is decided by the nostril deciding means 11 is stored in the memory and is used to set the nostril areas during the nostril tracking mode.

(Third Embodiment)

Figure 17:
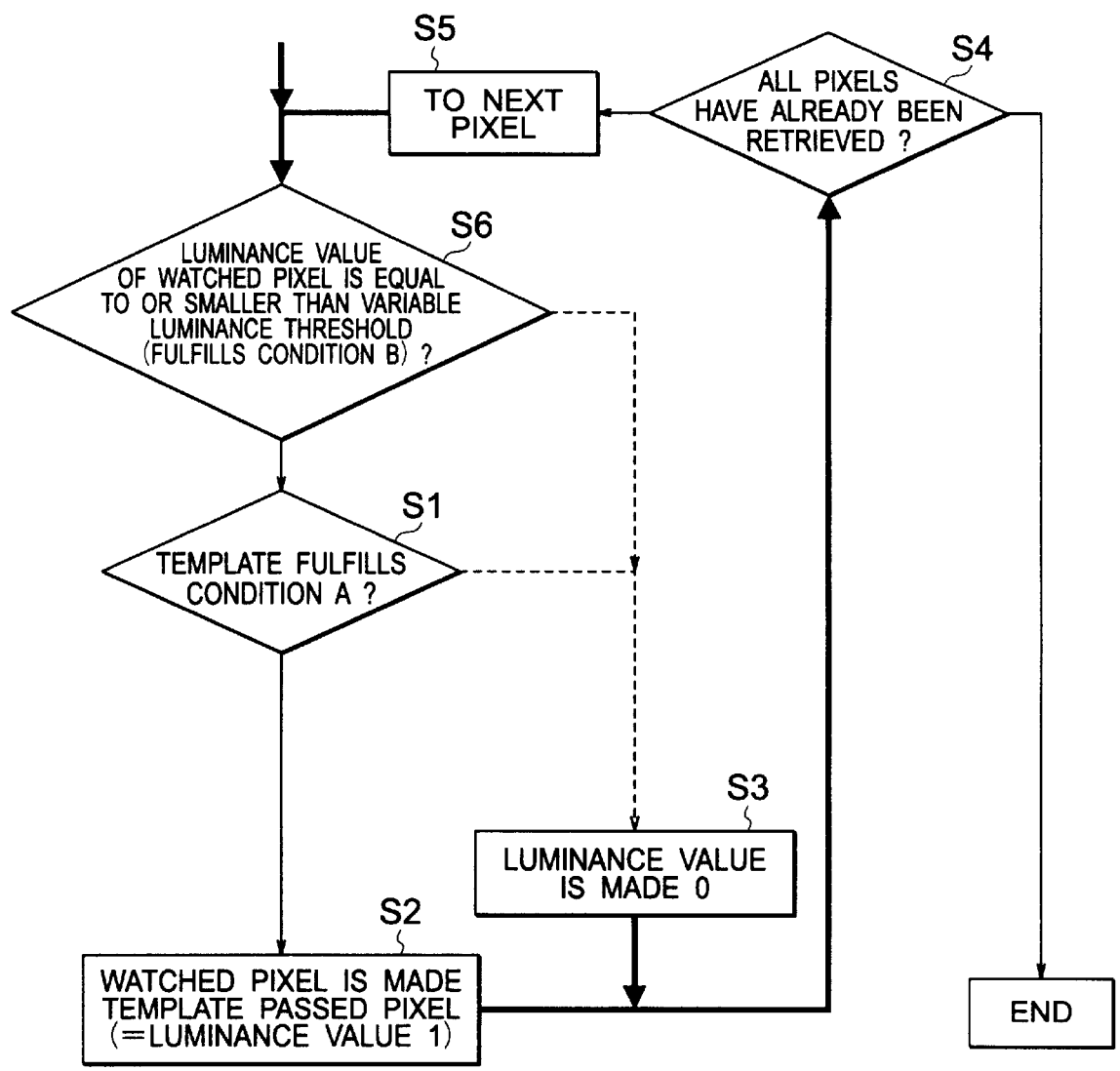
FIG. 17 is a flow chart for explaining the flow of the processing in an eye extracting means and a nostril extracting means according to a third embodiment of the present invention.
Figure 18A:
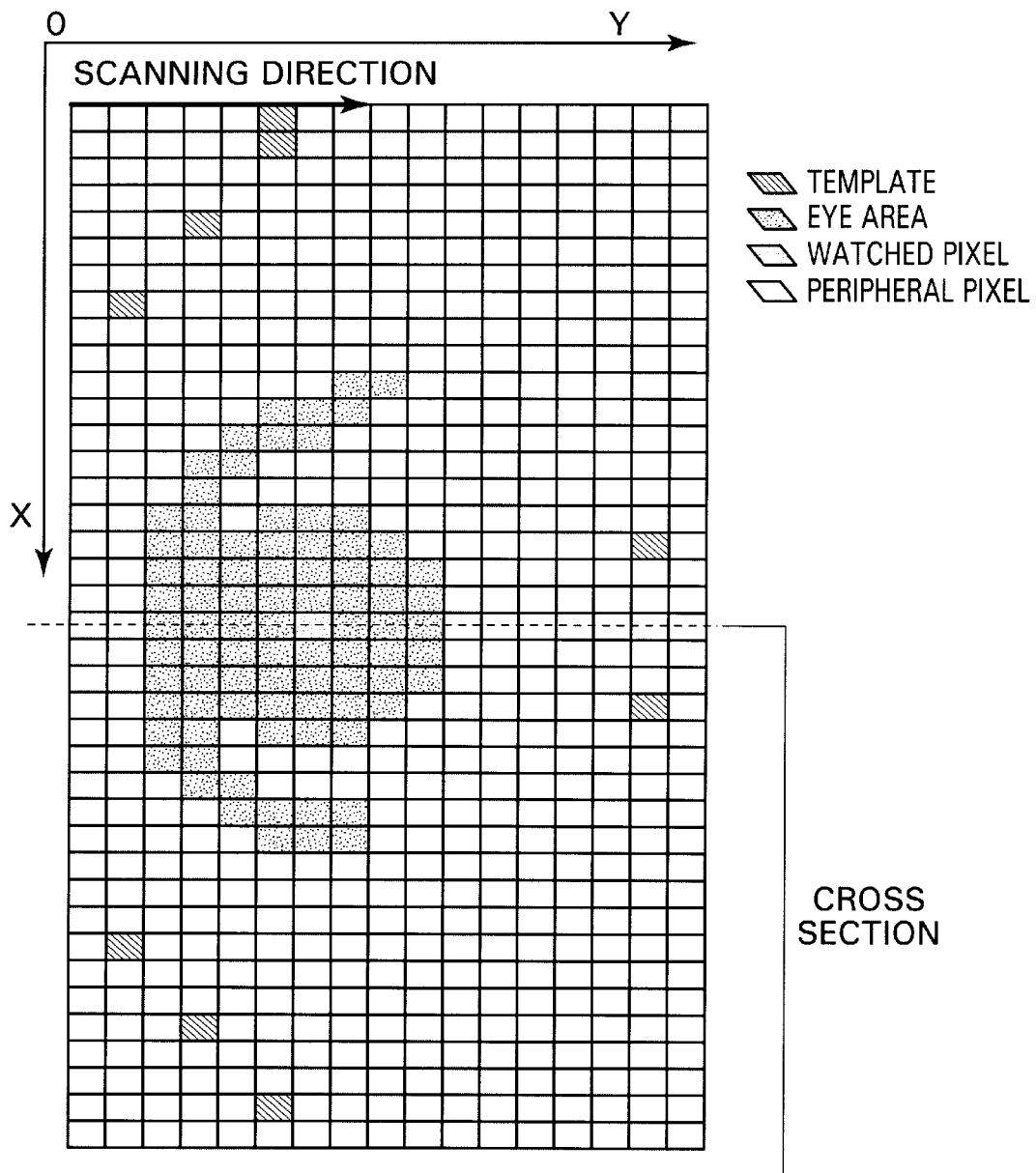
FIGS. 18(a) and 18(b) are diagrams for explaining the eye extracting means or the nostril extracting means according to the third embodiment of the present invention.
Figure 18B:
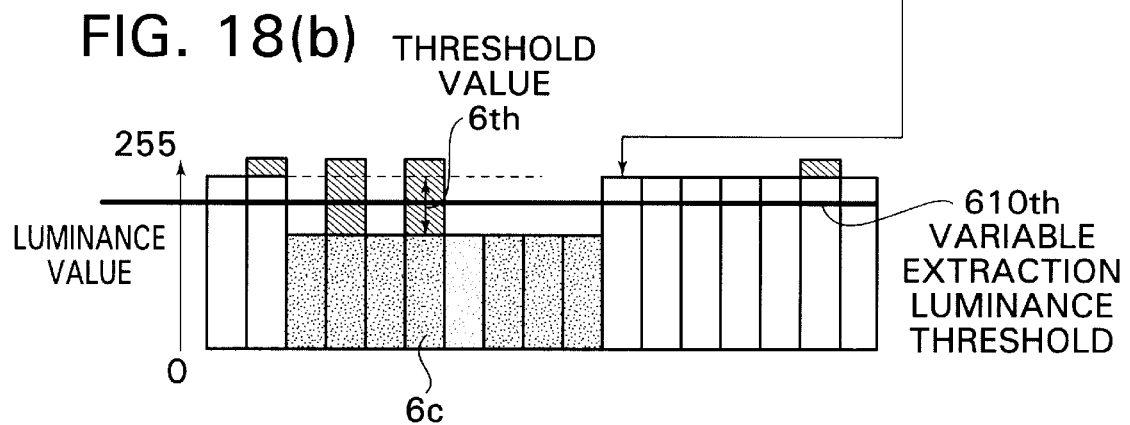

A third embodiment of the present invention is shown in FIGS. 17 and 18. The present embodiment is such that the variable extraction luminance threshold is used in the nostril candidate extracting means 10 and the eye candidate extracting means 6 of the above-mentioned first and second embodiments.

More specifically, as shown in a flow chart of FIG. 17, right before Step S1 of judging the condition of the template in the same manner as that in Step SI of FIG. 1, Step S6 is provided in which in the nostril candidate extracting means 10 and the eye candidate extracting means 6 of the above-mentioned first and second embodiments, the luminance value of the watched pixel is evaluated on the basis of the variable extraction luminance threshold (the image of the nostril and the image of the eye have the thresholds different from each other) to judge whether or not the evaluation based on the two-dimensional template is carried out. The criterion is, as shown in FIG. 18, the condition B (the luminance value of the watched pixel is equal to or smaller than the variable extraction luminance threshold 610th). In this connection, the reduction of the number of watched point pixels results in the processing speed being further increased. In addition, the variable extraction luminance threshold 610th is variably controlled on the basis of the luminance values of the pixels through which the two-dimensional template has passed until the last picture, whereby it is possible to obtain the value which is more suitable for the image than the case where the fixed value is adopted.

With respect to the variable extraction luminance threshold, for example, the estimated threshold is set. After the pixels of the eye (or the pixels of nostril) have been retrieved, if the extraction is possible, then it is judged that the threshold is proper and this threshold is continuously used. On the other hand, if it is judged that the extraction is impossible, then it is judged that the estimated threshold is improper, i.e., the pixels of the eye (or the nostril) are out of the range, and the threshold is relaxed step by step. In addition, while the threshold when carrying out the extraction may be used continuously as described above, if the threshold is reset by utilizing the mean luminance value, the maximum luminance value or the like of the pixels through which the two-dimensional template has passed, then the more proper threshold can be obtained.

(Fourth Embodiment)

Figure 19:
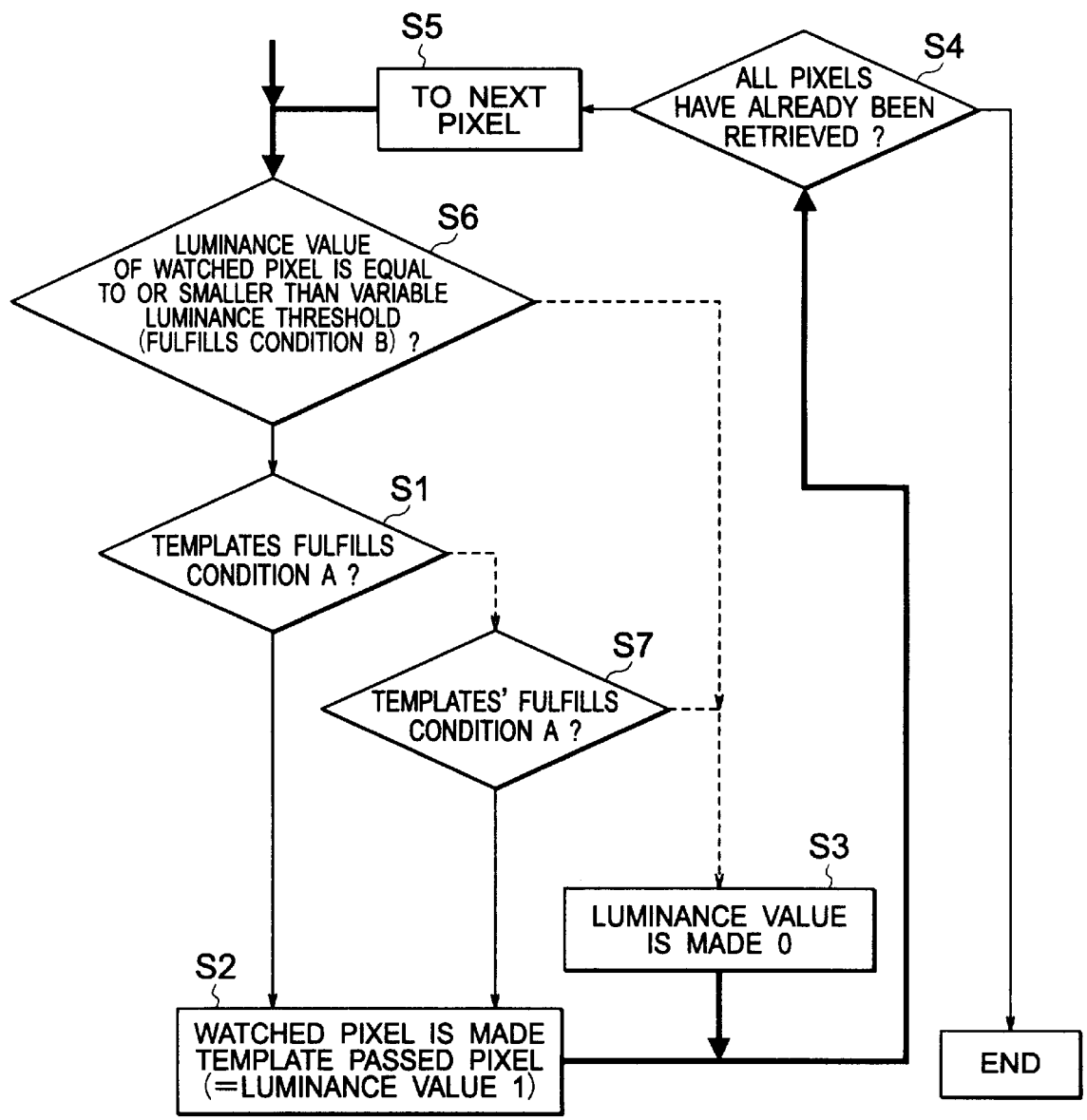
FIG. 19 is a flow chart for explaining the flow of the processing in an eye extracting means or a nostril extracting means according to a fourth embodiment of the present invention.

A fourth embodiment is shown in FIGS. 19 and 20. The present embodiment is such that a plurality of two-dimensional templates are employed in the nostril candidate extracting means 10 and the eye candidate extracting means 6 of the above-mentioned first, second and third embodiments.

While in the above-mentioned first, second and third embodiments, the two-dimensional templates 6t and 9t are employed in the nostril candidate extracting means 10 and the eye candidate extracting means 6, in the present embodiment, as shown in a flow chart of FIG. 19, if it is judged in Step S1 that the first two-dimensional templates 6t and 9t do not fulfill the condition A, then it is judged in Step S7 whether or not the next two-dimensional templates 6t' and 9t' fulfill the condition A. If it is judged in Step S7 that the next two-dimensional templates 6t' and 9t' fulfill the condition A, then the watched pixel is made the pixel through which the templates have passed.

Figure 20A:
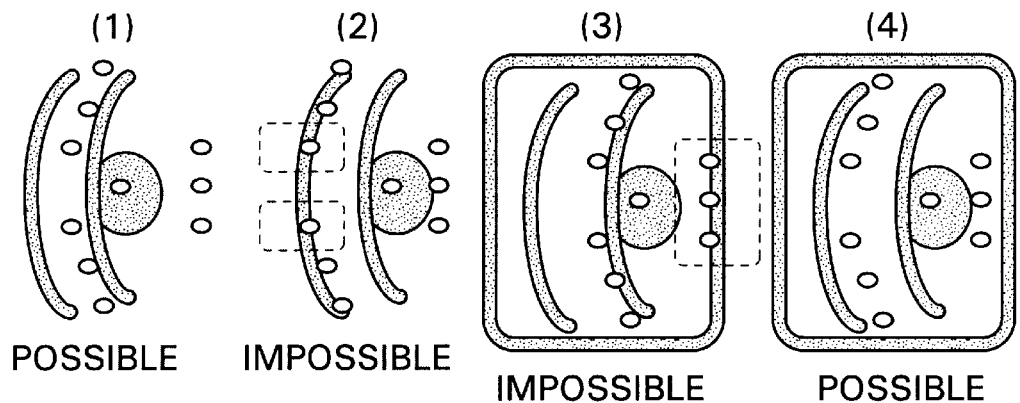
FIGS. 20(a) and 20(b) are diagrams respectively showing a template of the eye extracting means or the nostril extracting means according to the fourth embodiment of the present invention.

In addition, while a plurality of templates can be variously considered, for example, in FIG. 20(a), the distance between the watched pixel and the template pixel is only changed. As shown in parts (3) and (4) of FIG. 20(a), however, there is the possibility that since the distance between the watched point and the template on the lower side of the image of the eye is long, the passing is impossible (refer to a part (3) of FIG. 20(a)) depending on the position of the eyeglass frame when employing only the left-hand side template. In addition, as shown in parts (1) and (2) of FIG. 20(a), there is the possibility that when employing only the right-hand side template, for a person who has a small interval between the eyebrow and the eye, the passing becomes impossible (refer to the part (2) of FIG. 20(a)).

Figure 20B:
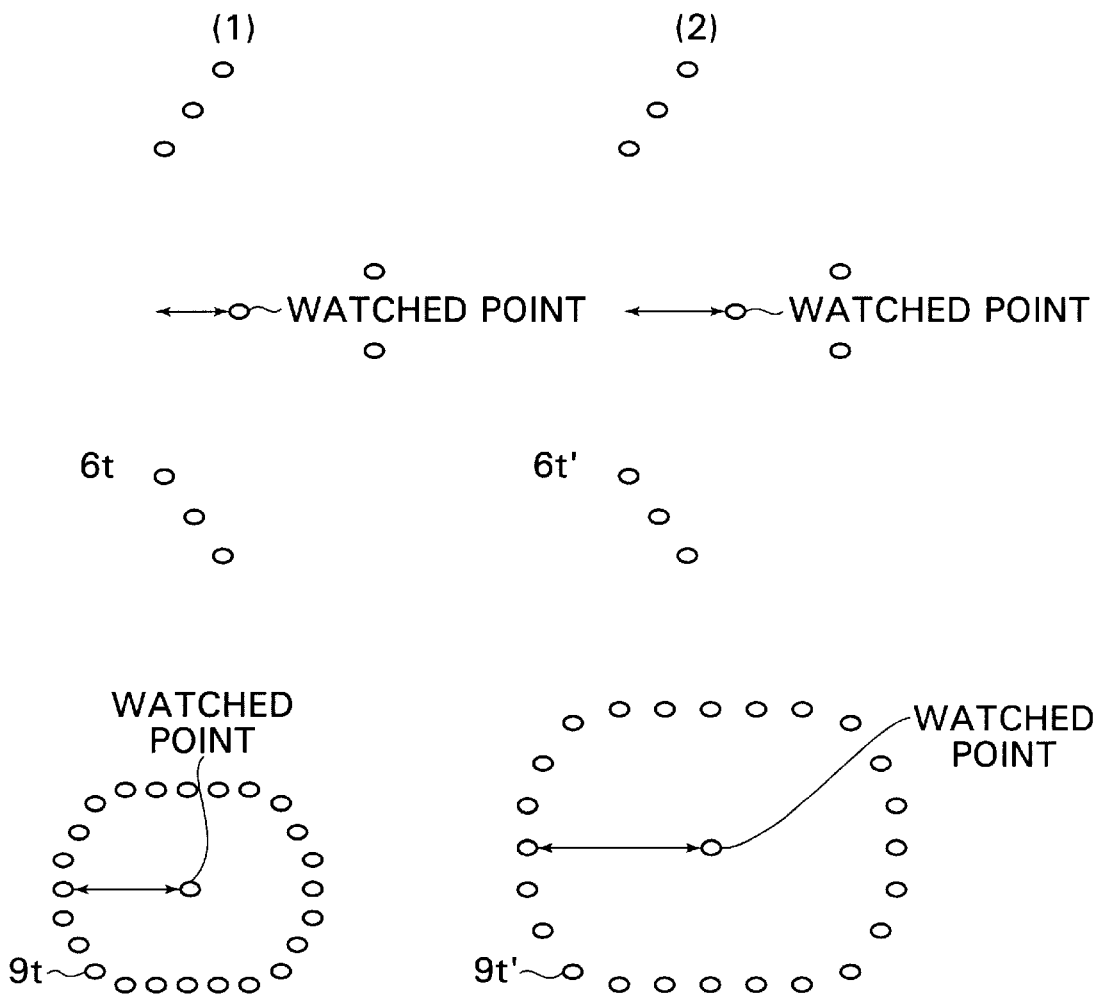

In other words, as shown in FIG. 20(b), the personal difference can be covered by the various sizes of the distance between the template and the watched point or the template.

While in this case, there are shown the two eye templates (1) and (2) in which the distances between the templates and the watched point are different from each other and the two nostril templates (3) and (4) which have the different sizes, the following contents are applied to either case. That is, it is also conceivable that two kinds of large and small templates for the eyes are provided to cover the personal difference, or the templates for the nostrils which are the same in the size and which have the different distances between the watched point and the templates to enable the nostrils to be detected even if there is the mustache. In this connection, while depending on the processing speed of the system, the kind of templates is not limited to the two, and hence if several kinds of templates are prepared, then the templates can cope with the many cases all the more.

(Fifth Embodiment)

Figure 21:
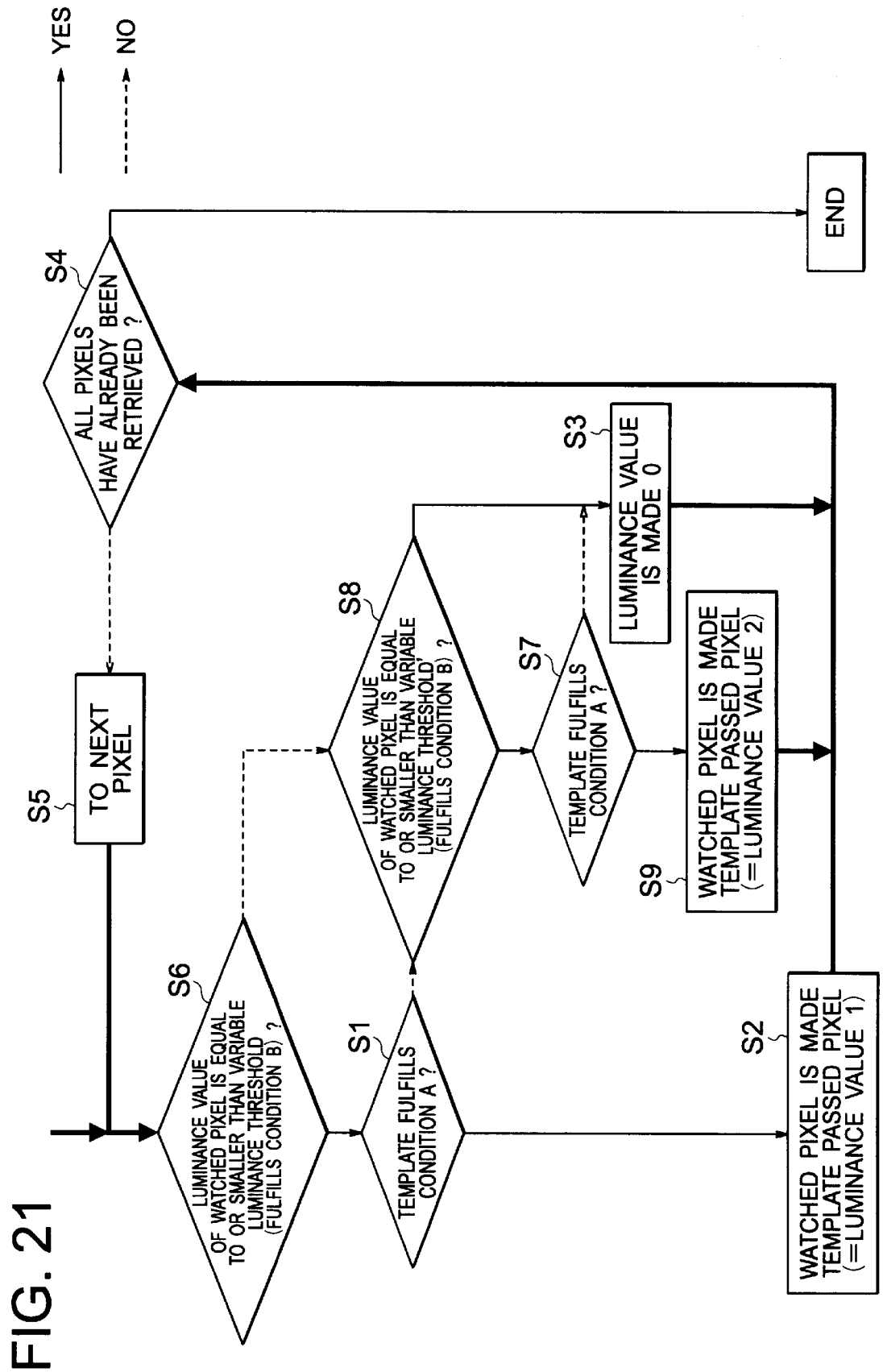
FIG. 21 is a flow chart for explaining the flow of the processing in an eye extracting means or a nostril extracting means according to a fifth embodiment of the present invention.

A fifth embodiment is shown in FIGS. 21 and 22. The present embodiment is such that a plurality of variable extraction luminance thresholds are employed in the nostril candidate extracting means 10 and the eye candidate extracting means 6 of the above-mentioned first to fourth embodiments.

In the fifth embodiment, a plurality of variable extraction luminance thresholds which are used to evaluate the luminance value of the watched pixel are prepared in the nostril candidate extracting means 10 and the eye candidate extracting means 6 of the above-mentioned first to third embodiments, thereby coping with either the speed-up which is provided by limiting the luminance range of the watched pixel or the luminance change of the input image. For example, when two variable extraction luminance thresholds 610th and 610th' (610th>610th') are prepared, if it is judged that the number of pixels which fulfill the condition B on the basis of the first variable extraction luminance threshold 610th is zero or small due to the luminance change of the input image, then the image is obtained in which the luminance value is converted into ternary number by carrying out again the evaluation using the second variable extraction luminance threshold 610th' which is smaller than the first variable extraction luminance threshold 610th. That is, as shown in a flow chart of FIG. 21, if the judgement result in Step S6 is "NO", then it is judged in Step S8 whether or not the luminance value of the watched pixel is equal to or smaller than the second variable extraction luminance threshold 610th'. On the other hand, if the judgement result in Step S6 is "YES", then it is judged in Step S7 whether or not the additional template fulfills the condition A. If the judgement result in Step S7 is "YES", then in Step S9, the watched pixel is made the template passed pixel to set the luminance value to 2. On the other hand, if the judgement result in Step S8 or Step S7 is "NO", then in Step S3, the luminance value of the watched pixel is set to "0".

Figure 22A:
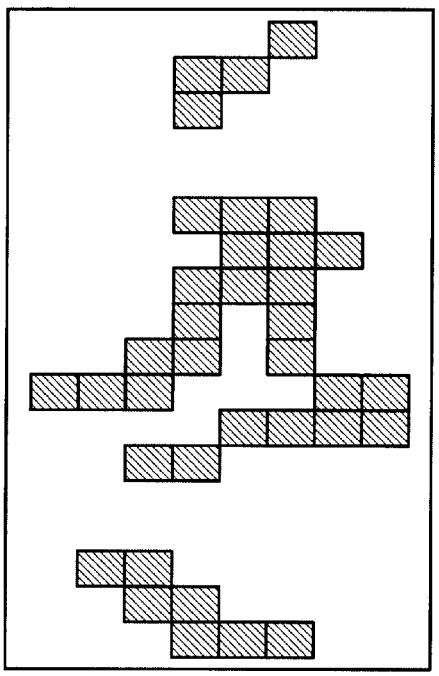
FIGS. 22(a) and 22(b) are diagrams for explaining the eye extracting means or the nostril extracting means according to the fifth embodiment of the present invention.
Figure 22B:
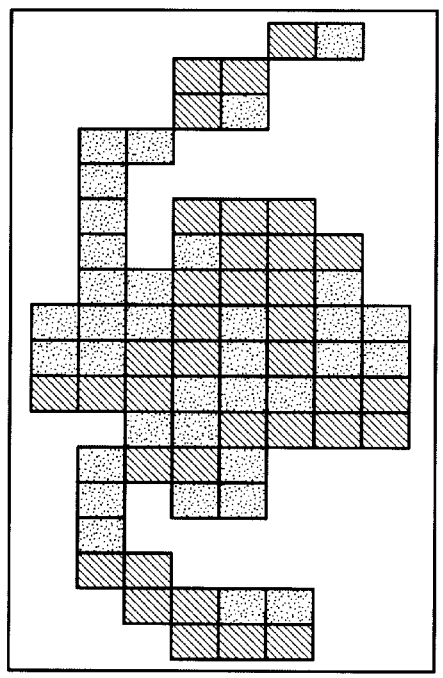

As shown in FIGS. 22(a) and 22(b), when the luminance value of the eye image is increased due to the glass reflection or the like, though when only the first variable extraction luminance threshold 610th is used, the image of the eye gets out of shape so that it is impossible to recognize the image of interest as the image of the eye (refer to FIG. 22(a)), the image of interest may be recognized as the image of the eye by using the second variable extraction luminance threshold 610th' in some cases (refer to FIG. 22(b)). The second variable extraction luminance threshold 610th' may be, similar to the variable extraction luminance threshold 610th of the third embodiment, controlled on the basis of the luminance values of the two-dimensional template passed pixels until the last picture, or may be controlled on the basis of the first variable extraction luminance threshold 610th.

(Sixth Embodiment)

Figure 23:
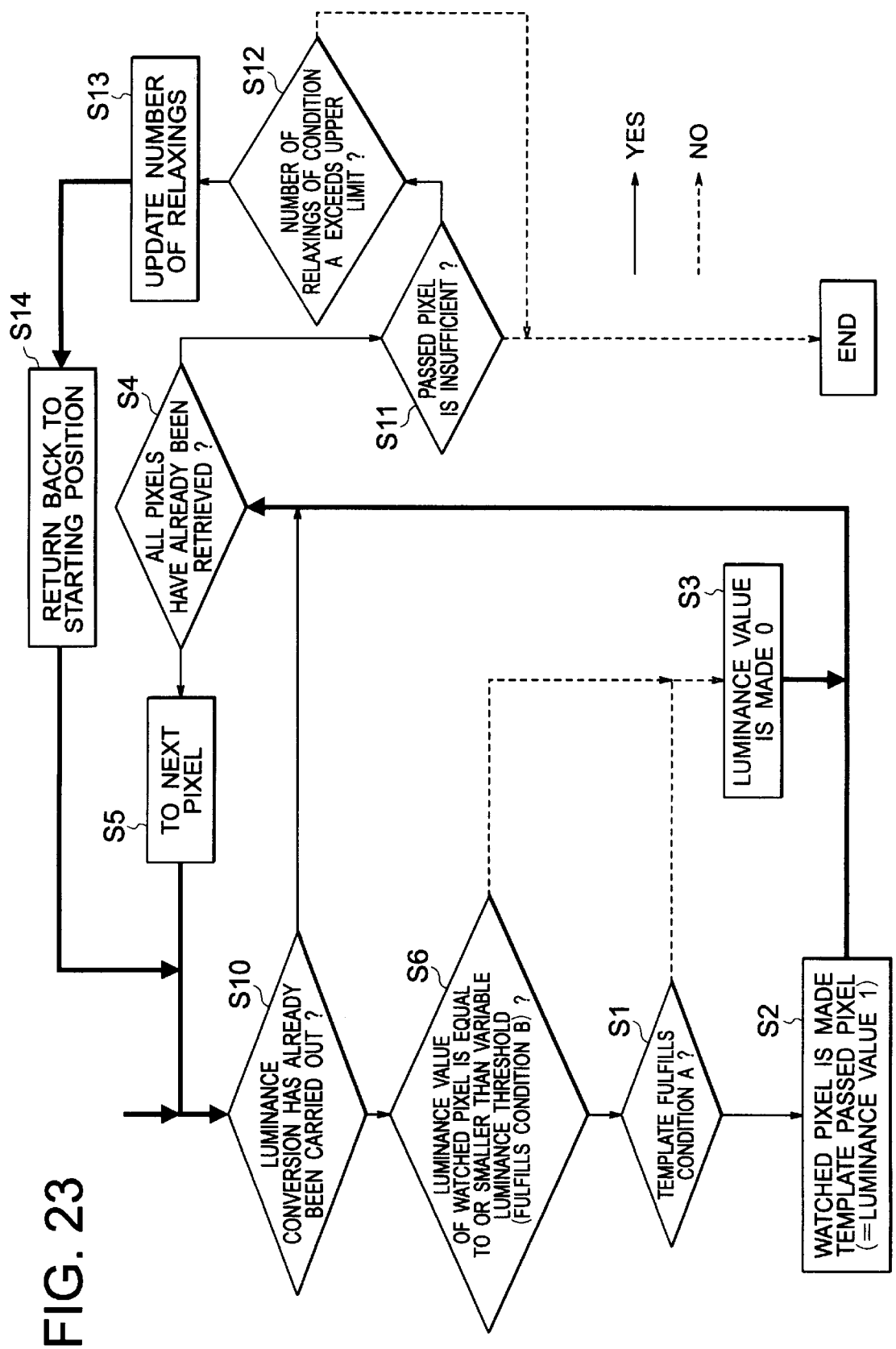
FIG. 23 is a flow chart useful in explaining the flow of the processing in an eye extracting means or a nostril extracting means according to a sixth embodiment of the present invention.
Figure 24:
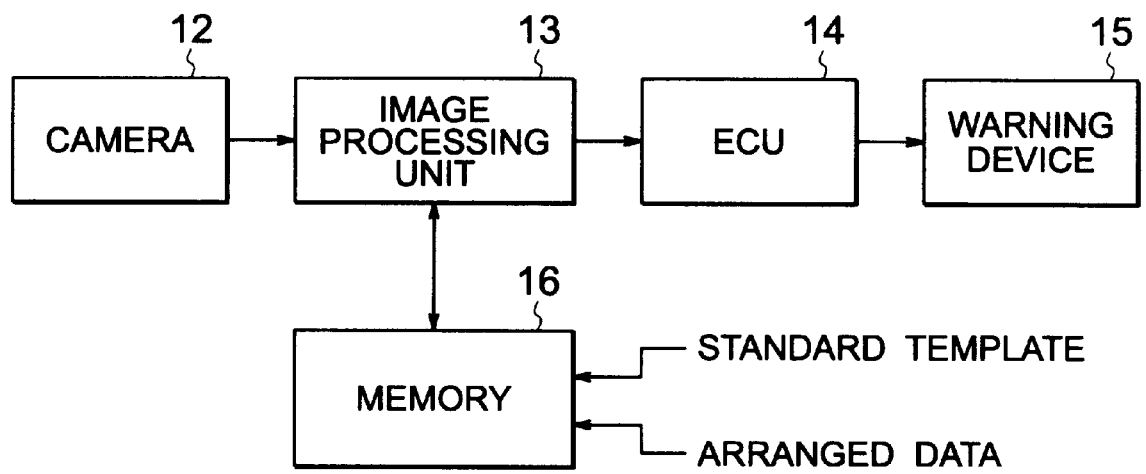
FIG. 24 is a block diagram showing an overall configuration of a prior art face image processing apparatus.
Figure 25:
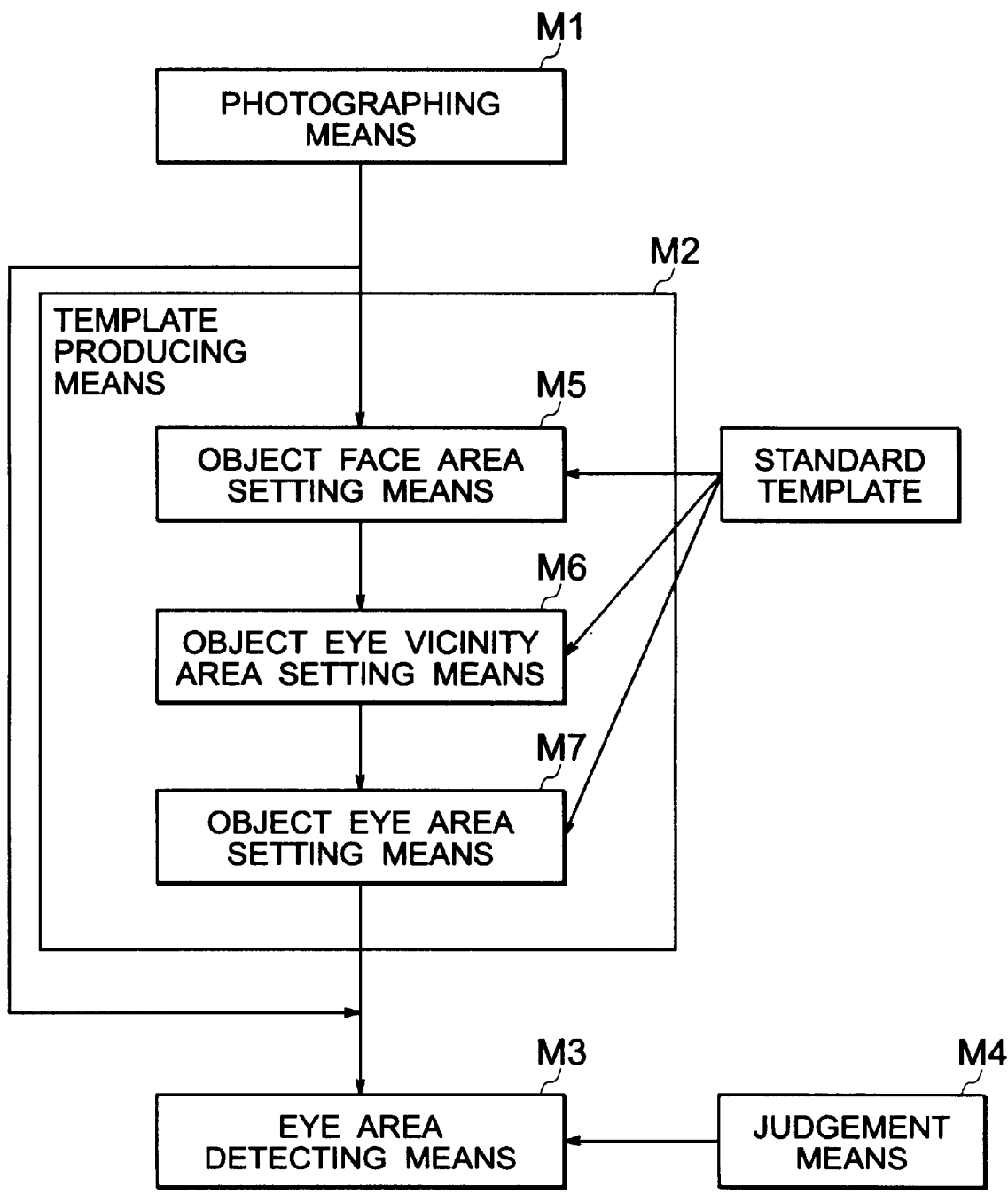
FIG. 25 is a block diagram for explaining a functional configuration of the prior art image processing apparatus.
Figure 26:
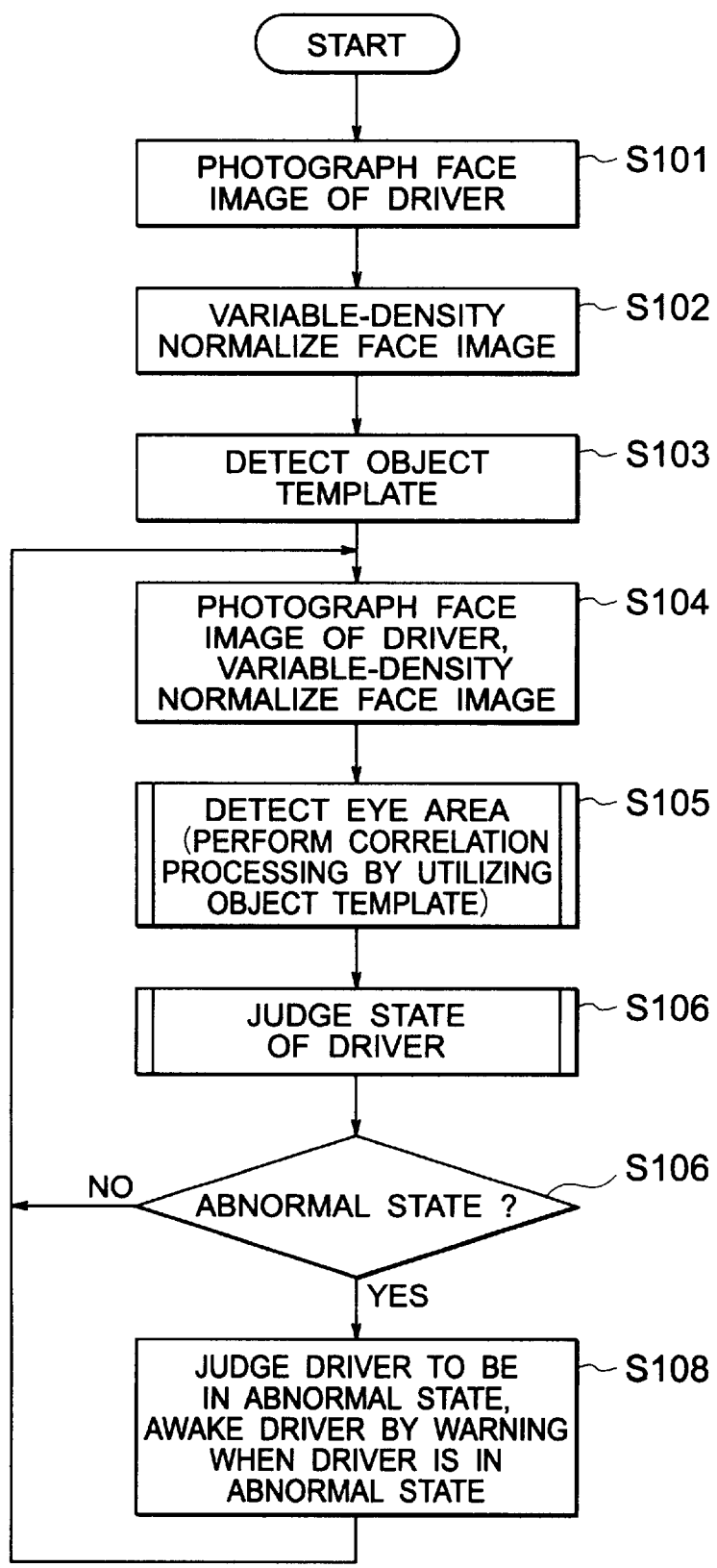
FIG. 26 is a flow chart for explaining the flow of the operation of the prior art image processing apparatus.

A sixth embodiment of the present invention is shown in FIG. 23. The sixth embodiment is such that in the nostril candidate extracting means 10 or the eye candidate extracting means 6 or both of the means 10 and 6 of the above-mentioned first to fifth embodiments, the two-dimensional template is relaxed in accordance with the degree of the image extraction.

In the nostril candidate extracting means 10 or the eye candidate extracting means 6 or both of the means 10 and 6 of the above-mentioned first to fifth embodiments, the situation in which it is difficult to fulfill the condition A is coped with by relaxing or modifying the requirements for the two-dimensional template. In the case where the number of passed pixels is zero or small when carrying out the extraction using both of the two-dimensional templates 6t and 9t, in the condition A, the number of template unpassed pixels is successively relaxed or modified as 0 point→1 point→2 points . . . every loop (the upper limit is set), thereby extracting the nostril candidate or the eye candidate or both of them.

More specifically, as shown in a flow chart of FIG. 23, first of all, it is judged in Step S10 whether or not the watched pixel has already been luminance-converted. If the judgement result in Step S10 is "YES", then the processing proceeds to Step S6. The processings up to Step S4 are the same as those of the flow chart shown in FIG. 4. On the other hand, if the judgement result in Step S10 is "NO", then the processing proceeds to Step S4 in which it is judged whether or not all of the pixels have already been retrieved. If the judgement result in Step S4 is "NO", then in Step S5, the processing target is changed over to the next pixel and then the processing is returned back to Step S10.

On the other hand, if the judgement result in Step S4 is "YES", then it is judged in Step S11 whether or nor the passed pixel is insufficient. If the judgement result in Step S11 is "YES", then it is judged in Step S12 whether or not the number of relaxings or modifications (the number of times of relaxings) of the condition A exceeds the predetermined upper limit. If the judgement result in Step S12 is "YES" (if so), then the number of relaxings is updated (e.g., the number of relaxings is incremented by 1) and then the processing is returned back to Step S10 as the starting position. On the other hand, if the judgement result in Step S11 or Step S12 is "NO", then the processing is completed.

As apparent from the foregoing, a face image processing apparatus according to one aspect of the present invention -includes: face image inputting means for inputting a face image; eye area setting means for estimating an area, in which an eye candidate is present, from the inputted face image; eye candidate extracting means for converting the eye candidate into the data having a plurality of luminance values within the eye area; and eye deciding means for deciding eyes within the extracted candidates and their positions. With this arrangement, the luminance conversion of the eye area is directly carried out using a two-dimensional template, whereby it is possible to extract the eye area at high speed without utilizing a nostril element or any of other auxiliary elements.

In addition, a face image processing apparatus according to another aspect of the present invention includes: face image inputting means for inputting a face image; nostril area setting means for estimating an area, in which a nostril candidate is present, from the inputted face image; nostril candidate extracting means for converting the nostril candidate into the data having a plurality of luminance values within the nostril area; nostril deciding means for deciding nostrils within the extracted nostril candidate; eye area setting means for estimating an area, in which an eye candidate is present, from the decided nostrils; eye candidate extracting means for converting the eye candidate into the data having a plurality of luminance values within the eye area; and eye deciding means for deciding the eyes within the candidate which has been extracted by the eye candidate extracting means and their positions. With this arrangement, the nostril extraction is carried out using a two-dimensional template and the area in which the image of the eyes is present is estimated using the images of the nostrils thus extracted, whereby it is possible to extract the eye area with high accuracy.

In a preferred form of the invention, either the nostril candidate extracting means or the eye candidate extracting means carries out the simple matching in relative luminance between a watched pixel and its peripheral pixels using a two-dimensional template and at least one threshold which are previously set. Accordingly, since using the two-dimensional template eliminates necessity of using the correlation operation in the general template matching, it is possible to extract the face elements with high accuracy and at high speed.

In another preferred form of the invention, either the nostril candidate extracting means or the eye candidate extracting means limits an object, for which the matching is carried out, further using a variable extraction luminance threshold. Thus, since the variable extraction luminance threshold is used together with the two-dimensional template to limit the area for which the two-dimensional template is used, it is possible to extract the face elements at higher speed.

In still another preferred form of the invention, either the nostril candidate extracting means or the eye candidate extracting means employs a plurality of variable extraction luminance thresholds or two-dimensional templates. Accordingly, since a plurality of two-dimensional templates are used together with a plurality of variable extraction luminance thresholds to cover the distinction in the face element due to the personal difference, it is possible to extract the face elements with higher accuracy.

In yet another preferred form of the invention, either the nostril candidate extracting means or the eye candidate extracting means relaxes the two-dimensional template in accordance with the degree of the image extraction. Thus, since the two-dimensional template is relaxed in accordance with the degree of the image extraction, the face elements can be extracted with higher accuracy in correspondence to the changes in the accessory information (the glass reflection, the hair of the head or the like).

While the present invention has been particularly shown and described with reference to the preferred embodiments, it will be understood that the various changes and modifications will occur to those skilled in the art without departing from the scope and true spirit of the invention. The scope of the invention is therefore to be determined solely by the appended claims.

What is claimed is:

1. A face image processing apparatus comprising:
   face image inputting means for inputting a face image;
   eye area setting means for estimating an area, in which an eye candidate is present, from the inputted face image;
   eye candidate extracting means for converting the eye candidate into the data having a plurality of luminance values within the eye area; and
   eye deciding means for deciding eye s within the extracted candidates and their positions.

2. A face image processing apparatus according to claim 1 wherein either said nostril candidate extracting means or said eye candidate extracting means carries out a simple matching in relative luminance between a watched pixel and its peripheral pixels using a two-dimensional template and at least one threshold which are previously set.

3. A face image processing apparatus according to claim 1, wherein either said nostril candidate extracting means or said eye candidate extracting means limits an object, for which the matching is carried out, further using a variable extraction luminance threshold.

4. A face image processing apparatus according to claim 1, wherein either said nostril candidate extracting means or said eye candidate extracting means employs a plurality of variable extraction luminance thresholds or two-dimensional templates.

5. A face image processing apparatus according to claim 1, wherein either said nostril candidate extracting means or said eye candidate extracting means relaxes the two-dimensional template in accordance with the degree of the image extraction.

6. A face image processing apparatus comprising:
   face image inputting means for inputting a face image;
   nostril area setting means for estimating an area, in which a nostril candidate is present, from the inputted face image;
   nostril candidate extracting means for converting the nostril candidate into the data having a plurality of luminance values within the nostril area;
   nostril deciding means for deciding nostrils within the extracted nostril candidate;
   eye area setting means for estimating an area, in which an eye candidate is present, from the decided nostrils;
   eye candidate extracting means for converting the eye candidate into the data having a plurality of luminance values within the eye area; and
   eye deciding means for deciding the eyes within the candidate which has been extracted by said eye candidate extracting means and their positions.

7. A face image processing apparatus according to claim 2, wherein either said nostril candidate extracting means or said eye candidate extracting means carries out a simple matching in relative luminance between a watched pixel and its peripheral pixels using a two-dimensional template and at least one threshold which are previously set.

8. A face image processing apparatus according to claim 6, wherein either said nostril candidate extracting means or said eye candidate extracting means limits an object, for which the matching is carried out, further using a variable extraction luminance threshold.

9. A face image processing apparatus according to claim 6, wherein either said nostril candidate extracting means or said eye candidate extracting means employs a plurality of variable extraction luminance thresholds or two-dimensional templates.

10. A face image processing apparatus according to claim 6, wherein either said nostril candidate extracting means or said eye candidate extracting means relaxes the two-dimensional template in accordance with the degree of the image extraction.

* * * * *